US012344666B2

(12) United States Patent
Imoukhuede et al.

(10) Patent No.: US 12,344,666 B2
(45) Date of Patent: Jul. 1, 2025

(54) PDGF MUTANTS AND METHODS OF USE THEREOF

(71) Applicants: Washington University, St. Louis, MO (US); The Board of Trustees of the University of Illinois, Urbana, IL (US)

(72) Inventors: Princess Imoukhuede, St. Louis, MO (US); Erik Procko, Urbana, IL (US)

(73) Assignees: Washington University, St. Louis, MO (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 17/836,684

(22) Filed: Jun. 9, 2022

(65) Prior Publication Data

US 2023/0050038 A1 Feb. 16, 2023

Related U.S. Application Data

(60) Provisional application No. 63/208,799, filed on Jun. 9, 2021.

(51) Int. Cl.

| | |
|---|---|
| ***A61K 38/18*** | (2006.01) |
| ***A61P 27/02*** | (2006.01) |
| ***A61P 35/00*** | (2006.01) |
| ***C07K 16/22*** | (2006.01) |

(52) U.S. Cl.

CPC .......... *C07K 16/22* (2013.01); *A61K 38/1858* (2013.01); *A61P 27/02* (2018.01); *A61P 35/00* (2018.01); *C07K 2317/76* (2013.01)

(58) Field of Classification Search

CPC .................................................. A61K 38/1858

See application file for complete search history.

(56) References Cited

U.S. PATENT DOCUMENTS

| | | | | |
|---|---|---|---|---|
| 5,128,321 | A * | 7/1992 | Murray ................ | C07K 14/005 530/300 |
| 5,326,695 | A | 7/1994 | Andersson et al. | |
| 5,512,545 | A | 4/1996 | Brown et al. | |
| 5,905,142 | A | 5/1999 | Murray | |
| 6,350,731 | B1 | 2/2002 | Jehanli et al. | |

FOREIGN PATENT DOCUMENTS

| | | | | |
|---|---|---|---|---|
| WO | WO-2016115506 A1 * | 7/2016 | ............. | A61P 17/06 |

OTHER PUBLICATIONS

Papanas and Maltezos (Clinical Interventions in Aging, 2008, vol. 3, pp. 233-240) (Year: 2008).*

Chen, S., et al., "Quantification of VEGFRs, NRP1, and PDGFRs on Endothelial Cells and Fibroblasts Reveals Serum, Intra-Family Ligand, and Cross-Family Ligand Regulation," 2015, Cellular and Molecular Bioengineering, 8/3:383-403, 23 pages.

Chen, P-H., et al., "Platelet-Derived Growth Factors and Their Receptors: Structural and Functional Perspectives," 2013, Biochim Biophys Acta, 1834/10:2176-2186, 25 pages.

Clements, J.M., et al., "Two PDGF-B Chain Residues, Arginine-27 and Isoleucine 30, Mediate Receptor Binding and Activation," 1991, The EMBO Journal, 10/13:4113-4120, 8 pages.

Collins, T., et al., "Cultured Human Endothelial Cells Express Platelet-Derived Growth Factor A Chain," 1987, AJP, 7-12, 6 pages.

Kreysing, J., et al., "Identification of Three Amino Acid Residues in the B-Chain of Platelet-Derived Growth Factor with Different Importance for Binding to PDGF Alpha- and Beta-Receptors," 1996, FEBS Letters, 385:181-184, 4 pages.

Larochelle, W.J., et al., "Five PDGF B Amino Acid Substitutions Convert PDGF A to a PDGF B-like Transforming Molecule," 1992, J Biol Chem, 267/24:17074-17077, 4 pages.

Mamer, S.B., et al., "Discovery of High-Affinity PDGF-VEGFR Interactions: Redefining RTK Dynamics, " 2017, Scientific Reports, 7/1:16439, DOI:10.1038/S41598-017-16610-z, 14 pages.

Östman, A., et al., "Identification of Three Amino Acids in the Platelet-derived Growth Factor (PDGF) B-Chain that are Important for Binding to the PDGF Bet-Receptor," 1991, J Biol Chem, 266/16:10073-10077, 5 pages.

Pennock, S., et al., "Vascular Endothelial Growth Factor A Competitively Inhibits Platelet-Derived Growth Factor (PDFG)-Dependent Activation of PDGF Receptor and Subsequent Signaling Events and Cellular Responses," 2012, Mol Cell Biol, 32/10:1955-1966, 12 pages.

Shim, A.H-R., et al., "Structures of a Platelet-dDerived Growth Factor/Propeptide Complex and a Platelet Derived Growth Factor/Receptor Complex," 2010, PNAS, 107/25:11307-11312, 6 pages.

* cited by examiner

*Primary Examiner* — Karen A. Canella

(74) *Attorney, Agent, or Firm* — Stinson LLP

(57) ABSTRACT

Isolated polypeptides having enhanced affinity for a PDGF receptor and/or a VEGF receptor are provided. Compositions comprising the polypeptides and methods of use thereof are also provided.

20 Claims, 20 Drawing Sheets

Specification includes a Sequence Listing.

FIG. 5A

```
SEQ ID
  NO:                         10        20        30           60          80           100
                              |         |         |            |           |            |
  1   Wild type    ...PAMIAECKTRTEVFEISRRLIDRTNAN...CNNRNVQCR...RKIEIVRKK...HLACKCETVAA
                         E   N    L R   N   I          Y           F            R  K
  2   Clone-01     ...PAMIAECKTRTYLFRISRNLIDRTNAN...CNNRYVQCR...RKIEFVRKK...HLACRCETVAA
  3   Clone-02     ...PAMIAECNTRTYVFRISRNLIDRTNAN...CNNRNVQCR...RKIEFVRKK...HLACRCEKVAA
  4   Clone-03     ...PAMIAECKTRTELFRISRNLIDRTNAN...CNNRYVQCR...RKIEFVRKK...HLACKCEKVAA
  5   Clone-04     ...PAMEAECKTRTEVFRISRNLIDITNAN...CNNRYVQCR...RKIEFVRKK...HLACRCETVAA
  5   Clone-05     ...PAMEAECKTRTEVFRISRNLIDITNAN...CNNRYVQCR...RKIEFVRKK...HLACRCETVAA
  6   Clone-06     ...PAMIAECKTRTYLFEISRNLIDITNAN...CNNRYVQCR...RKIEFVRKK...HLACKCEKVAA
  7   Clone-07     ...PAMIAECKTRTEVFEISRNLIDRTNAN...CNNRNVQCR...RKIEFVRKK...HLACKCETVAA
  8   Clone-08     ...PAMIAECKTRTYLFRISRNLIDRTNAN...CNNRYVQCR...RKIEIVRKK...HLACRCETVAA
  9   Consensus    ...PAMIAECKTRTEVFRISRNLIDRTNAN...CNNRYVQCR...RKIEFVRKK...HLACRCETVAA
```

FIG. 5B

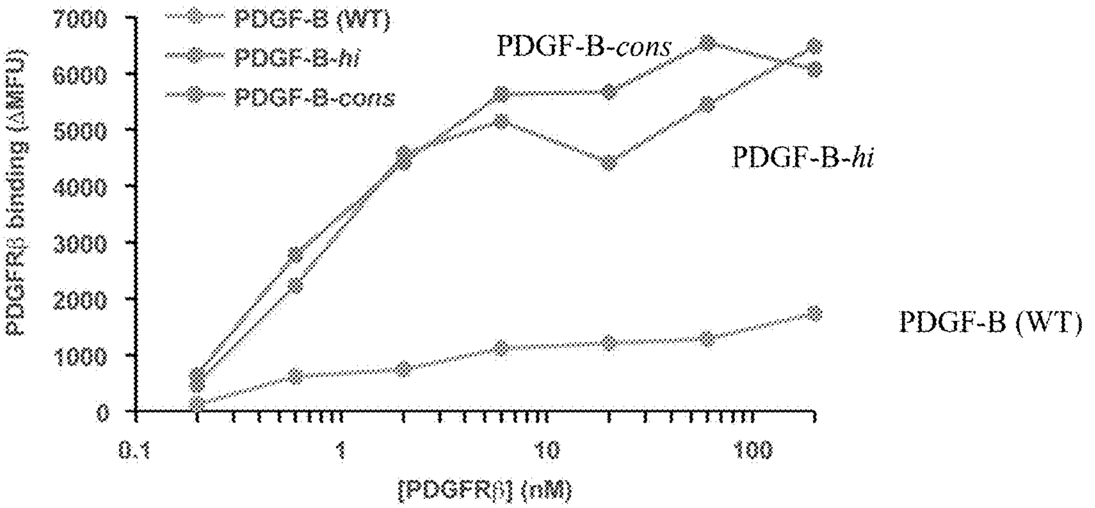

FIG. 5C

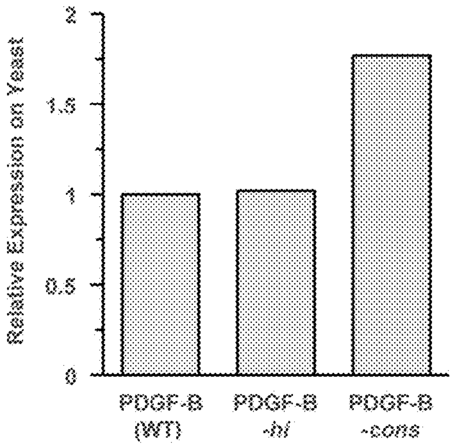

FIG. 11
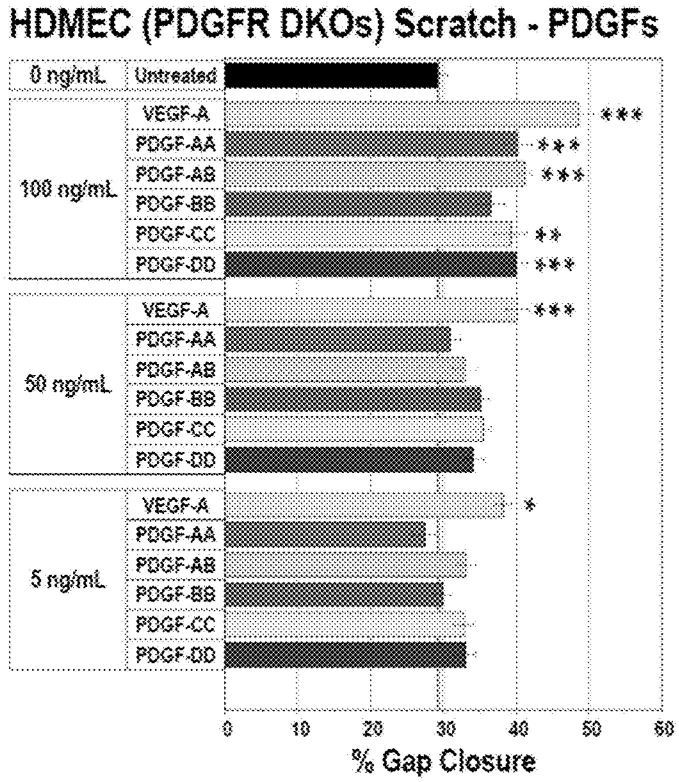
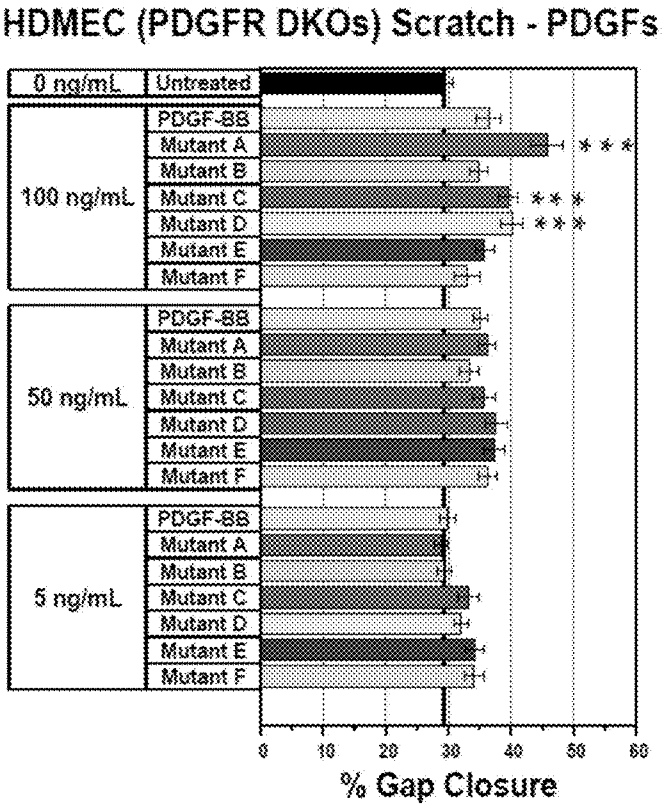

```
                        SEQUENCE LISTING

<160> NUMBER OF SEQ ID NOS: 12

<210> SEQ ID NO 1
<211> LENGTH: 104
<212> TYPE: PRT
<213> ORGANISM: Homo sapiens

<400> SEQUENCE: 1

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala
            100


<210> SEQ ID NO 2
<211> LENGTH: 104
<212> TYPE: PRT
<213> ORGANISM: Artificial Sequence
<220> FEATURE:
<223> OTHER INFORMATION: Synthetic

<400> SEQUENCE: 2

Ser Leu Gly Ser Leu Thr Ile Ala Glu Pro Ala Met Ile Ala Glu Cys
1               5                   10                  15

Lys Thr Arg Thr Glu Leu Phe Arg Ile Ser Arg Asn Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Tyr Val Gln Cys Arg Pro Thr Gln
    50                  55                  60

Val Gln Leu Arg Pro Val Gln Val Arg Lys Ile Glu Phe Val Arg Lys
65                  70                  75                  80

Lys Pro Ile Phe Lys Lys Ala Thr Val Thr Leu Glu Asp His Leu Ala
                85                  90                  95

Cys Arg Cys Glu Thr Val Ala Ala
            100


<210> SEQ ID NO 3
<211> LENGTH: 104
<212> TYPE: PRT
<213> ORGANISM: Artificial Sequence
```

```
<220> FEATURE:
<223> OTHER INFORMATION: Synthetic

<400> SEQUENCE: 3

Ser Leu Gly Ser Leu Thr Ile Ala Glu Pro Ala Met Ile Ala Glu Cys
1               5                   10                  15

Asn Thr Arg Thr Glu Val Phe Arg Ile Ser Arg Asn Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Phe Val Arg Lys
65                  70                  75                  80

Lys Pro Ile Phe Lys Lys Ala Thr Val Thr Leu Glu Asp His Leu Ala
                85                  90                  95

Cys Arg Cys Glu Lys Val Ala Ala
            100


<210> SEQ ID NO 4
<211> LENGTH: 104
<212> TYPE: PRT
<213> ORGANISM: Artificial Sequence
<220> FEATURE:
<223> OTHER INFORMATION: Synthetic

<400> SEQUENCE: 4

Ser Leu Gly Ser Leu Thr Ile Ala Glu Pro Ala Met Ile Ala Glu Cys
1               5                   10                  15

Lys Thr Arg Thr Glu Leu Phe Arg Ile Ser Arg Asn Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Tyr Val Gln Cys Arg Pro Thr Gln
    50                  55                  60

Val Gln Leu Arg Pro Val Gln Val Arg Lys Ile Glu Phe Val Arg Lys
65                  70                  75                  80

Lys Pro Ile Phe Lys Lys Ala Thr Val Thr Leu Glu Asp His Leu Ala
                85                  90                  95

Cys Lys Cys Glu Lys Val Ala Ala
            100


<210> SEQ ID NO 5
<211> LENGTH: 104
<212> TYPE: PRT
<213> ORGANISM: Artificial Sequence
<220> FEATURE:
<223> OTHER INFORMATION: Synthetic

<400> SEQUENCE: 5

Ser Leu Gly Ser Leu Thr Ile Ala Glu Pro Ala Met Glu Ala Glu Cys
1               5                   10                  15

Lys Thr Arg Thr Glu Val Phe Arg Ile Ser Arg Asn Leu Ile Asp Ile
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Tyr Val Gln Cys Arg Pro Thr Gln
    50                  55                  60
```

-continued

```
Val Gln Leu Arg Pro Val Gln Val Arg Lys Ile Glu Phe Val Arg Lys
65                  70                  75                  80

Lys Pro Ile Phe Lys Lys Ala Thr Val Thr Leu Glu Asp His Leu Ala
                85                  90                  95

Cys Arg Cys Glu Thr Val Ala Ala
            100
```

<210> SEQ ID NO 6
<211> LENGTH: 104
<212> TYPE: PRT
<213> ORGANISM: Artificial Sequence
<220> FEATURE:
<223> OTHER INFORMATION: Synthetic

<400> SEQUENCE: 6

```
Ser Leu Gly Ser Leu Thr Ile Ala Glu Pro Ala Met Ile Ala Glu Cys
1               5                   10                  15

Lys Thr Arg Thr Glu Leu Phe Glu Ile Ser Arg Asn Leu Ile Asp Ile
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Tyr Val Gln Cys Arg Pro Thr Gln
    50                  55                  60

Val Gln Leu Arg Pro Val Gln Val Arg Lys Ile Glu Phe Val Arg Lys
65                  70                  75                  80

Lys Pro Ile Phe Lys Lys Ala Thr Val Thr Leu Glu Asp His Leu Ala
                85                  90                  95

Cys Lys Cys Glu Lys Val Ala Ala
            100
```

<210> SEQ ID NO 7
<211> LENGTH: 104
<212> TYPE: PRT
<213> ORGANISM: Artificial Sequence
<220> FEATURE:
<223> OTHER INFORMATION: Synthetic

<400> SEQUENCE: 7

```
Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Asn Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Phe Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala
            100
```

<210> SEQ ID NO 8
<211> LENGTH: 104
<212> TYPE: PRT
<213> ORGANISM: Artificial Sequence
<220> FEATURE:
<223> OTHER INFORMATION: Synthetic -continued

<400> SEQUENCE: 8

Ser Leu Gly Ser Leu Thr Ile Ala Glu Pro Ala Met Ile Ala Glu Cys
1               5                   10                  15

Lys Thr Arg Thr Glu Leu Phe Arg Ile Ser Arg Asn Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Tyr Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Arg Cys Glu Thr Val Ala Ala
            100

<210> SEQ ID NO 9
<211> LENGTH: 104
<212> TYPE: PRT
<213> ORGANISM: Artificial Sequence
<220> FEATURE:
<223> OTHER INFORMATION: Synthetic

<400> SEQUENCE: 9

Ser Leu Gly Ser Leu Thr Ile Ala Glu Pro Ala Met Ile Ala Glu Cys
1               5                   10                  15

Lys Thr Arg Thr Glu Val Phe Arg Ile Ser Arg Asn Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Tyr Val Gln Cys Arg Pro Thr Gln
    50                  55                  60

Val Gln Leu Arg Pro Val Gln Val Arg Lys Ile Glu Phe Val Arg Lys
65                  70                  75                  80

Lys Pro Ile Phe Lys Lys Ala Thr Val Thr Leu Glu Asp His Leu Ala
                85                  90                  95

Cys Arg Cys Glu Thr Val Ala Ala
            100

<210> SEQ ID NO 10
<211> LENGTH: 104
<212> TYPE: PRT
<213> ORGANISM: Artificial Sequence
<220> FEATURE:
<223> OTHER INFORMATION: Synthetic

<400> SEQUENCE: 10

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Phe Val Arg Lys
65                  70                  75                  80

-continued

```
Lys Pro Ile Phe Lys Lys Ala Thr Val Thr Leu Glu Asp His Leu Ala
                85                  90                  95

Cys Lys Cys Glu Thr Val Ala Ala
            100


<210> SEQ ID NO 11
<211> LENGTH: 104
<212> TYPE: PRT
<213> ORGANISM: Artificial Sequence
<220> FEATURE:
<223> OTHER INFORMATION: Synthetic

<400> SEQUENCE: 11

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Tyr Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala
            100


<210> SEQ ID NO 12
<211> LENGTH: 104
<212> TYPE: PRT
<213> ORGANISM: Artificial Sequence
<220> FEATURE:
<223> OTHER INFORMATION: Synthetic

<400> SEQUENCE: 12

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
            20                  25                  30

Thr Asn Ala Asn Phe Leu Val Trp Pro Pro Cys Val Glu Val Gln Arg
        35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Arg Cys Glu Thr Val Ala Ala
            100
```

PDGF MUTANTS AND METHODS OF USE THEREOF

REFERENCE TO RELATED APPLICATIONS

This application claims benefit of U.S. provisional application Ser. No. 63/208,799, filed Jun. 9, 2021, the entire disclosure of which is incorporated herein by reference.

STATEMENT REGARDING FEDERALLY SPONSORED RESEARCH OR DEVELOPMENT

This invention was made with Government support under 1653925 awarded by the National Science Foundation. The government has certain rights to the invention.

INCORPORATION OF SEQUENCE LISTING

A paper copy of the Sequence Listing and a computer readable form of the Sequence Listing containing the file named "3510075.005702 Sequence Listing_ST25," which is 12,212 bytes in size (as measured in MICROSOFT WINDOWS® EXPLORER) and was created on Jun. 8, 2022, are provided herein and are herein incorporated by reference. This Sequence Listing consists of SEQ ID NOs: 1-12.

FIELD OF THE INVENTION

The present invention relates to isolated polypeptides having an affinity for a PDGF receptor and/or a VEGF receptor. Compositions comprising the polypeptides and methods of use thereof are also provided.

BACKGROUND OF THE INVENTION

Vascular endothelial growth factor receptors (VEGFRs) are key mediators of angiogenesis, vasculogenesis, and lymphangiogenesis. Their signaling involves selective binding of five human VEGF ligands [VEGF-A, VEGF-B, VEGF-C, VEGF-D, and placental GF (PlGF)] to their associated receptors. Modulating VEGF signaling presents a useful therapeutic target; however, VEGF as a pro-angiogenic agent has not successfully treated peripheral artery or coronary artery diseases. Anti-VEGF therapy has been applied towards cancers, yet they only have moderate effects on patient survival, due to both intrinsic and acquired resistance/relapse.

Recently, a cross-signaling effect has been observed where related growth factors (e.g., platelet derived growth factor or PDGF) have been found to bind and activate VEGF—sometimes at a level greater than native VEGF. This cross-signaling phenomenon suggests that PDGF may be a suitable alternative to VEGF in therapeutics that modulate VEGFR/PDGFR signaling. However, suitable versions of PDGF that have sufficiently high affinity towards the receptors are still needed.

Accordingly, there is a need for PDGF variants having increased affinity for PDGF and VEGF receptors. These variants would be useful in therapeutics targeting these receptors.

BRIEF SUMMARY OF THE INVENTION

Provided herein are isolated polypeptides having an amino acid sequence comprising at least about 70% of SEQ ID NO: 1, wherein the polypeptides bind to a PDGF receptor and/or a VEGF receptor and wherein the polypeptides comprise at least one amino acid substitution resulting in a higher binding affinity to the receptor than a wild-type PDGF or VEGF polypeptide.

Also provided are pharmaceutical compositions comprising the polypeptide and a pharmaceutically appropriate carrier.

Still further provided is a method of modulating VEGF and PDGF signaling in a cell, the method comprising applying a polypeptide provided herein to the cell.

Also provided is a method of treating a disease or condition associated with abnormal PDGF and/or VEGF signaling in a subject in need thereof, the method comprising administering the polypeptide to the subject.

Other objects and features will be in part apparent and in part pointed out hereinafter.

BRIEF DESCRIPTION OF THE DRAWINGS

FIG. 5A shows the sequence alignment of PDGF-B clones isolated from a combinatorial yeast display library that was sorted for high PDGFRβ binding. The wild type PDGF-B sequence (SEQ ID NO: 1) is at top in black, and mutations included in the library are immediately below in bold. Clones-04 and 05 are identical, and are renamed PDGF-B-hi (SEQ ID NO: 5). The consensus sequence (called PDGF-B-cons, SEQ ID NO: 9) is in bold at the bottom.

FIG. 5B shows binding of soluble PDGFRβ to PDGF-B wild type, PDGF-B-hi, or PDGF-B-cons expressed on yeast surface, measured by flow cytometry. Yeast were gated for equivalent levels of PDGF-B expression.

FIG. 5C shows relative expression of PDGF-B variants on the yeast surface.

FIG. 11 depicts a PDGFRα/β double knockout human dermal microvascular endothelial cell (HDMEC) scratch assay measuring percent gap closure after ligand stimulation. HDMEC migration was measured using wound-healing assays at 0 and 50 hours post scratch. Wound area was measured using ImageJ, and the percent gap closure was calculated. Significance was determined using a one-way ANOVA, and pairwise comparisons were made using the Tukey Test. * indicates a value significantly different than the untreated condition. # indicates a mutant significantly different from PDGF-BB at the same concentration. * or # indicates $p<0.05$.  or ## indicates $p<0.01$. * or ### indicates $p<0.001$. N>7 for *, and N=20 for #.

DETAILED DESCRIPTION OF THE INVENTION

Figure 1A:
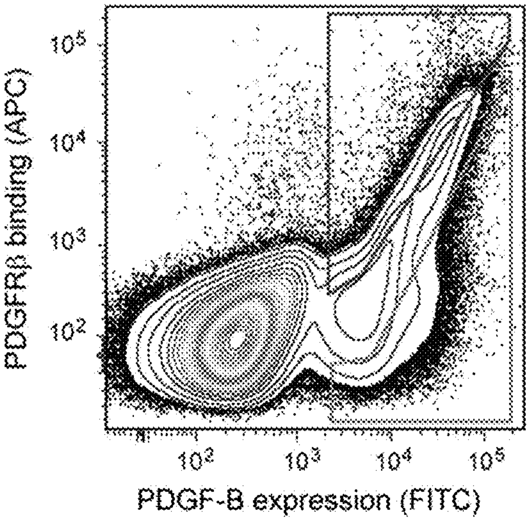
FIG. 1A is a plot showing flow cytometry analysis of yeast displaying a SSM library of PDGF-B. PDGFRβ binding (y-axis) correlates with surface PDGF-B expression (x-axis). Yeast expressing higher affinity PDGF-B mutants (top gate) or lower affinity PDGF-B mutants (bottom gate) were collected by fluorescence activated cell sorting (FACS).

Provided herein are isolated polypeptides having an enhanced affinity for a PDGF receptor and/or a VEGF receptor. The isolated polypeptides can have an amino acid sequence comprising at least about 70% of SEQ ID NO: 1, wherein the polypeptide binds to a PDGF receptor and/or a VEGF receptor, and wherein the polypeptide comprises at least one amino acid substitution resulting in a higher binding affinity to the receptor than a wild-type PDGF or VEGF polypeptide.

The polypeptide can comprise at least one amino acid substitution at position 13, 17, 21, 22, 24, 28, 32, 57, 71, 77, 78, 98, or 101.

For example, the amino acid substitution at position 13 can be selected from the group consisting of I13E, I13F, and I13Y. For example, the amino acid substitution can comprise I13E.

The amino acid substitution at position 17 can be selected from the group consisting of K17A, K17S, K17T, K17N, K17I, K17Q, K17D, K17E, and K17G. For example, the amino acid substitution can comprise K17N.

The amino acid substitution at position 21 can be selected from the group consisting of E21F, E21Y, E21A, and E21V. For example, the amino acid substitution can comprise E21Y.

The amino acid substitution at position 22 can be selected from the group consisting of V22M, V22L, and V22T. For example, the amino acid substitution can comprise V22L.

The amino acid substitution at position 24 can be selected from the group consisting of E24M, E24L, E241, E24V, E24A, E24R, and E24T. For example, the amino acid substitution can comprise E24R.

The amino acid substitution at position 28 can be selected from the group consisting of R28N, R28Q, R28S, R28T, R28A, R28W, and R28G. For example, the amino acid substitution can comprise R28N.

The amino acid substitution at position 32 can be selected from the group consisting of R32T, R32V, and R32I. For example, the amino acid substitution can comprise R32I.

The amino acid substitution at position 57 can be selected from the group consisting of N57Y, N57W, and N57F. For example, the amino acid substitution can comprise N57Y.

The amino acid substitution at position 71 can be Q71M.

The amino acid substitution at position 77 can be I77F.

The amino acid substitution at position 78 can be selected from the group consisting of V78W, V78R, and V78K.

The amino acid substitution at position 98 can be K98R.

The amino acid substitution at position 101 can be selected from the group consisting of T101K and T101R. For example, the amino acid substitution can comprise T101K.

The polypeptide can comprise more than one amino acid substitution as compared to reference SEQ ID NO: 1. For example, the polypeptide can comprise any of the following combinations of amino acid substitutions:

(a) V22L, E24R, R28N, N57Y, 177F and K98R
(b) K17N, E24R, R28N, I77F, K98R and T101K
(c) V22L, E24R, R28N, N57Y, 177F and T101K
(d) I13E, E24R, R28N, N57Y, 177F and K98R
(e) V22L, R28N, N57Y, 177F and T101K
(f) R28N and I77F
(g) V22L, E24R, R28N, N57Y and K98R
(h) E24R, R28N, N57Y, 177F and K98R In various embodiments, the polypeptide can comprise an amino acid sequence selected from the group consisting of SEQ ID NOs: 2-12. For ease of reference, these sequences are described in Table 1, below. In the table, residues at locations identified above are bolded, and the % identity of the resulting sequence relative to WT is indicated.

TABLE 1

PDGF-B Wild Type, Mutant, and Consensus Sequences

| Description | SEQ ID NO | Sequence | Mutations relative to WT | % Identity Relative to WT |
|---|---|---|---|---|
| WT | SEQ ID NO: 1 | SLGSLTIAEPAMIA<br>ECKTRTEVFEISRR<br>LIDRTNANFLVWP<br>PCVEVQRCSGCCN<br>NRNVQCRPTQVQL<br>RPVQVRKIEIVRK<br>KPIFKKATVTLED<br>HLACKCETVAA | none | 100% |
| Clone-01/ Mutant A | SEQ ID NO: 2 | SLGSLTIAEPAMIA<br>ECKTRTELFRISRN<br>LIDRTNANFLVWP | V22L, E24R, R28N, N57Y, I77F, K98R | 94% |

TABLE 1-continued

PDGF-B Wild Type, Mutant, and Consensus Sequences

| Description | SEQ ID NO | Sequence | Mutations relative to WT | % Identity Relative to WT |
|---|---|---|---|---|
| | | PCVEVQRCSGCCN NR**Y**VQCRPTQVQL RPVQVRKIE**F**VRK KPIFKKATVTLED HLAC**R**CE**T**VAA | | |
| Clone-02 | SEQ ID NO: 3 | SLGSLTIAEPAM**I**A EC**N**TRTE**V**F**R**ISR**N** LID**R**TNANFLVWP PCVEVQRCSGCCN NR**N**VQCRPTQVQL RPVQVRKIE**F**VRK KPIFKKATVTLED HLAC**R**CE**K**VAA | K17N, E24R, R28N, I77F, K98R, T101K | 94% |
| Clone-03/ Mutant D | SEQ ID NO: 4 | SLGSLTIAEPAM**I**A EC**K**TRTE**LF**R**ISR**N** LID**R**TNANFLVWP PCVEVQRCSGCCN NR**Y**VQCRPTQVQL RPVQVRKIE**F**VRK KPIFKKATVTLED HLAC**K**CE**K**VAA | V22L, E24R, R28N, N57Y, I77F, T101K | 94% |
| Clone-04/ 05/PDGF-B- hi/Mutant B | SEQ ID NO: 5 | SLGSLTIAEPAM**E** AEC**K**TRTE**V**F**R**ISR **N**LID**I**TNANFLVW PPCVEVQRCSGCC NNR**Y**VQCRPTQV QLRPVQVRKIE**F**V RKKPIFKKATVTL EDHLAC**R**CE**T**VAA | I13E, E24R, R28N, N57Y, I77F, K98R | 94% |
| Clone-06 | SEQ ID NO: 6 | SLGSLTIAEPAM**I**A EC**K**TRTE**LF**E**ISR**N** LID**I**TNANFLVWPP CVEVQRCSGCCNN R**Y**VQCRPTQVQLR PVQVRKIE**F**VRKK PIFKKATVTLEDHL AC**K**CE**K**VAA | V22L, R28N, N57Y, I77F, T101K | 94% |
| Clone-07 | SEQ ID NO: 7 | SLGSLTIAEPAM**I**A EC**K**TRTE**V**F**E**ISR**N** LID**R**TNANFLVWP PCVEVQRCSGCCN NR**N**VQCRPTQVQL RPVQVRKIE**F**VRK KPIFKKATVTLED HLAC**K**CE**T**VAA | R28N, I77F | 98% |
| Clone-08 | SEQ ID NO: 8 | SLGSLTIAEPAM**I**A EC**K**TRTE**LF**R**ISR**N** LID**R**TNANFLVWP PCVEVQRCSGCCN NR**Y**VQCRPTQVQL RPVQVRKIE**I**VRK KPIFKKATVTLED HLAC**R**CE**T**VAA | V22L, E24R, R28N, N57Y, K98R | 94% |
| Consensus/ PDGF-B- cons | SEQ ID NO: 9 | SLGSLTIAEPAM**I**A EC**K**TRTE**V**F**R**ISR**N** LID**R**TNANFLVWP PCVEVQRCSGCCN NR**Y**VQCRPTQVQL RPVQVRKIE**F**VRK KPIFKKATVTLED HLAC**R**CE**T**VAA | E24R, R28N, N57Y, I77F, K98R | 94% |
| Mutant E | SEQ ID NO: 10 | SLGSLTIAEPAM**I**A EC**K**TRTE**V**F**E**ISR**R** LID**R**TNANFLVWP PCVEVQRCSGCCN NR**N**VQCRPTQVQL RPVQVRKIE**F**VRK | I77F | 99% |

TABLE 1-continued

PDGF-B Wild Type, Mutant, and Consensus Sequences

| Description | SEQ ID NO | Sequence | Mutations relative to WT | % Identity Relative to WT |
|---|---|---|---|---|
| | | KPIFKKATVTLED HLACKCETVAA | | |
| Mutant F | SEQ ID NO: 11 | SLGSLTIAEPAMIA ECKTRTEVFEISRR LIDRTNANFLVWP PCVEVQRCSGCCN NRYVQCRPTQVQL RPVQVRKIEIVRK KPIFKKATVTLED HLACKCETVAA | N57Y | 99% |
| Mutant C | SEQ ID NO: 12 | SLGSLTIAEPAMIA ECKTRTEVFEISRR LIDRTNANFLVWP PCVEVQRCSGCCN NRNVQCRPTQVQL RPVQVRKIEIVRK KPIFKKATVTLED HLACRCETVAA | K98R | 99% |

In addition to the amino acid substitutions described above, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic amino acids and their amides (e.g., Aspartate, Glutamate, Asparagine, Glutamine).

Accordingly, the polypeptide provided may have a certain % sequence identity relative to wild-type. In various embodiments, the polypeptide has an amino acid sequence having at least 70%, at least 75%, at least 80%, at least 85%, at least 90%, at least 91%, at least 92%, at least 93%, at least 94%, at least 95%, at least 96%, at least 97%, or at least 98% sequence identity to SEQ ID NO: 1. In various embodiments, the polypeptide can have at least 94% or at least 98% sequence identity to SEQ ID NO: 1.

Dimers

PDGF binds its receptors as a dimer and an inability to form a dimer has been shown to reduce its binding ability. Accordingly, in various embodiments, two polypeptides described herein are provided as a dimer. The dimer can be a heterodimer or a homodimer—that is, it can comprise two polypeptides having identical amino acid substitutions relative to SEQ ID NO: 1 or two peptides having different substitutions relative to SEQ ID NO: 1.

In various embodiments, the individual polypeptides (or monomers) that comprise the dimer are separately expressed. They can be used as monomers or combined to form dimers. Methods for preparing the polypeptides (e.g., expression systems) are described in the next section. The dimers can be assembled extracellularly (e.g., in a buffer, cell media, or cell culture system) and then purified. Alternatively, the dimers can be assembled intracellularly by expressing more than one peptide in an expression system and can then be purified.

Functional dimers can be identified by standard methods in the art where the non-reduced sample is run on a Western blot to determine if the dimer size conforms to expected sizing. Alternatively, since PDGF only activates PDGF-Receptor when it is a dimer, activity assays can be used to determine the level of dimerization.

Methods of Preparing Polypeptides

Methods for producing polypeptides of the invention are known in the art. For example, DNA molecules encoding the polypeptides can be chemically synthesized. Synthetic DNA molecules can be ligated to other appropriate nucleotide sequences, including, e.g., expression control sequences, to produce conventional gene expression constructs encoding the desired polypeptide. Production of defined gene constructs is within routine skill in the art.

Nucleic acids encoding desired polypeptides can be incorporated (ligated) into expression vectors, which can be introduced into host cells through conventional transfection or transformation techniques. Illustrative host cells are *E. coli* cells, human embryonic kidney (HEK) cells, Pichiapastoris cells, Baculovirus cells, Chinese hamster ovary (CHO) cells, HeLa cells, baby hamster kidney (BHK) cells, and monkey kidney cells (COS). Transformed host cells can be grown under conditions that permit the host cells to express the genes that encode the polypeptides described herein.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The gene can also be cloned into an expression vector for inducible expression by positioning the engineered gene downstream within a suitable operon, e.g. Lac, and be induced by the appropriate corresponding agent, e.g. IPTG. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon, and, optionally, may contain enhancers, and various introns. The gene construct can be introduced into eukaryotic host cells using conventional techniques. The host cells express the polypeptides that may be attached to a moiety having another function (e.g., cytotoxicity). The host cells may express proteases for proteolytic processing and maturation of the desired polypeptide. For example, a PRO domain in a PDGF ligand can be proteolytically removed during maturation in mammalian expression systems. Alternatively, PDGF ligands may be expressed or chemically synthesized without a PRO domain.

A polypeptide described herein can be produced by growing (culturing) a host cell transfected with an expression vector encoding the polypeptide, under conditions that permit expression of the polypeptide. Following expression, the polypeptide can be harvested and purified or isolated using techniques known in the art, e.g., using affinity tags such as glutathione-S-transferase (GST) and histidine tags. Other isolation techniques include gel filtration/Ni affinity and ion-exchange column chromatography.

Therefore, in various embodiments, a nucleic acid is provided, the nucleic acid comprising a nucleotide sequence encoding the polypeptide described herein. The skilled person will appreciate that functional variants of these nucleic acid molecules are also intended to be a part of the present invention. Functional variants are nucleic acid sequences that can be directly translated, using the standard genetic code, to provide an amino acid sequence identical to that translated from the parental nucleic acid molecules.

In various embodiments, an expression vector is provided comprising one or more of the nucleic acids described herein. Vectors can be derived from plasmids such as: F, F1, RP1, Col, pBR322, TOL, Ti, etc; cosmids; phages such as lambda, lambdoid, M13, Mu, P1, P22, Qβ, T-even, T-odd, T2, T4, T7 etc; or plant viruses. Vectors can be used for cloning and/or expression of the polypeptides of the invention and might even be used for gene therapy purposes. Vectors comprising one or more nucleic acid molecules according to the invention operably linked to one or more expression-regulating nucleic acid molecules are also covered by the present invention. The choice of the vector is dependent on the recombinant procedures followed and the host used. Introduction of vectors in host cells can be effected by inter alia calcium phosphate transfection, virus infection, DEAE-dextran mediated transfection, lipofectamine transfection or electroporation. Vectors may be autonomously replicating or may replicate together with the chromosome into which they have been integrated. Preferably, the vectors contain one or more selection markers. The choice of the markers may depend on the host cells of choice. They include, but are not limited to, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the human binding molecules as described above operably linked to one or more nucleic acid molecules encoding proteins or peptides that can be used to isolate the human binding molecules are also covered by the invention. These proteins or peptides include, but are not limited to, glutathione-S-transferase, maltose binding protein, metal-binding polyhistidine, green fluorescent protein, luciferase and beta-galactosidase.

The expression vector may be transfected into a host cell to induce the translation and expression of the nucleic acid into the polypeptide. Therefore, a host cell is provided comprising any expression vector described herein. Host cells include, but are not limited to, cells of mammalian, plant, insect, fungal or bacterial origin. Bacterial cells include, but are not limited to, cells from Gram-positive bacteria or Gram-negative bacteria such as several species of the genera *Escherichia*, such as *E. coli*, and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or bolistic gene transfer. Additionally, a suitable expression system can be a baculovirus system. Expression systems using mammalian cells, such as Chinese Hamster Ovary (CHO) cells, COS cells, BHK cells, and NSO cells are preferred in the present invention. Mammalian cells provide expressed proteins with posttranslational modifications that are most similar to natural molecules of mammalian origin. Since the present invention deals with molecules that may have to be administered to humans, a completely human expression system where the host cells are human cells could be used. Examples of human cells are inter alia HeLa, 911, AT1080, A549, HEK293 and HEK293T cells.

Further a method is provided for producing a polypeptide having enhanced affinity for a PDGF receptor, the method comprising growing a host cell as described herein under conditions so that the host cell expresses the polypeptide and purifying the polypeptide.

Compositions

Also provided are pharmaceutical compositions comprising at least one polypeptide described herein and a pharmaceutically acceptable carrier.

Pharmaceutical compositions containing one or more of the polypeptides described herein can be formulated in any conventional manner. Proper formulation is dependent in part upon the route of administration selected. Routes of administration include, but are not limited to parenteral (e.g., intravenous, intra-arterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration. Preferably, the composition is administered parenterally or topically.

Pharmaceutically acceptable excipients for use in the compositions of the present invention are selected based upon a number of factors including the particular compound used, and its concentration, stability and intended bioavailability; the subject, its age, size and general condition; and the route of administration.

The pharmaceutical compositions can also be formulated for parenteral administration, e.g., formulated for injection via intravenous, intra-arterial, subcutaneous, rectal, subcutaneous, intramuscular, intraorbital, intracapsular, intraspinal, intraperitoneal, or intrasternal routes. Dosage forms suitable for parenteral administration include solutions, suspensions, dispersions, emulsions or any other dosage form that can be administered parenterally.

The pharmaceutical compositions can also be formulated for topical administration. Dosage forms suitable for topical administration include creams, lotions, suspensions, emulsions, dispersions, or any other dosage form that can be administered topically.

The pharmaceutical compositions can also be formulated for sustained delivery for a given route of administration. Dosage forms suitable for sustained delivery include microspheres, nanospheres, hydrogels, or any other dosage form that can be administered for sustained delivery. The dosage can also be incorporated into dressings for wounds, such as those used in dentistry and surgery.

Pharmaceutically acceptable excipients are identified, for example, in The Handbook of Pharmaceutical Excipients, (American Pharmaceutical Association, Washington, D.C., and The Pharmaceutical Society of Great Britain, London, England, 1968). Additional excipients can be included in the pharmaceutical compositions of the invention for a variety of purposes. These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, non-volatile silicones, adhesives, bulking agents, flavorings, sweeteners, adsorbents, binders, disintegrating agents, lubricants, coating agents, and antioxidants.

Methods of Use

Also provided are methods of modulating PDGF and/or VEGF signaling in vitro and in vivo. For example, a method is provided for modulating PDGF and/or VEGF signaling in a cell, the method comprising applying a polypeptide described herein to the cell. In various embodiments, the method can comprise increasing PDGF or VEGF signaling in the cell. In other embodiments, the method can comprise decreasing PDGF or VEGF signaling in the cell. The cell may be one that naturally expresses either PDGFRs or VEGFRs. Alternatively, the cell may be transfected with a vector according to methods described above to express a PDGFR or VEGFR. The cell can be a bacterial, yeast, mammalian, or insect cell. In various embodiments, the cell is a human cell.

The ability of the polypeptide to increase or decrease PDGF/VEGF signaling can, in some cases, depend on its binding affinity for the receptor. For example, a polypeptide with elevated binding affinity for the receptor may bind more frequently, and thus increase signaling. However, if the polypeptide does not activate or only partially activates the receptor, but binds at a higher affinity, it may actually compete with normal PDGF/VEGF and reduce overall signaling. Accordingly, the polypeptides herein, which all bind to the PDGF or VEGF receptor with a higher affinity as compared to wild-type PDGF will be expected to increase or decrease PDGF/VEGF signaling, depending on the experimental context.

Accordingly, the method can comprise increasing PDGF signaling. Alternatively, the method can comprise increasing VEGF signaling. Alternatively, the method can comprise decreasing PDGF signaling. Or, the method can comprise decreasing VEGF signaling.

Various diseases and conditions are affected by disrupted or abnormal PDGF/VEGF signaling and the polypeptides and pharmaceutical compositions containing them as described herein may also be useful in treating these diseases or conditions in the subject. Accordingly, a method of treating a disease or condition associated with abnormal PDGF and/or VEGF signaling in a subject in need thereof is provided, the method comprising administering a polypeptide described herein (or a pharmaceutical composition containing the polypeptide) to the subject.

In various embodiments, the disease or condition may be associated with elevated PDGF and/or VEGF signaling and the polypeptide can decrease PDGF and/or VEGF signaling. For example, the disease may be selected from the group consisting of cancer, diabetic retinopathy and age-related macular degeneration.

In various embodiments, the disease or condition may be associated with decreased PDGF and/or VEGF signaling and the polypeptide can increase PDGF and/or VEGF signaling. As an example, wound healing processes often rely on the PDGF/VEGF signaling pathways. Accordingly, the method can be for treating wounds or enhancing wound healing.

In various embodiments, additional therapeutic agents may be provided alongside the polypeptides to enhance the therapeutic properties described herein. For example, the method to improve wound healing can further comprise administering becaplermin to the subject.

The polypeptide or composition comprising the polypeptide may be administered in whatever route most efficiently delivers the polypeptide to the target PDGF/VEGF receptors. As would be appreciated by one of skill in the art, the mode of administration will likely vary depending on the therapeutic goal. Accordingly, in various embodiments (e.g., when improving wound healing), the polypeptide may be administered topically. In other embodiments, the polypeptide may be administered parenterally.

Having described the invention in detail, it will be apparent that modifications and variations are possible without departing from the scope of the invention defined in the appended claims.

EXAMPLES

The following non-limiting examples are provided to further illustrate the present invention.

Example 1: Deep Mutational Scanning to Interrogate Ligand-Receptor Interactions The mature polypeptides of VEGF-C, PDGF-A, and PDGF-B bind to the soluble extracellular domains of VEGFR3, PDGFRα, and PDGFRβ, respectively, when expressed as fusions with Aga2p on the yeast surface. These interactions are known to be high affinity, and long glycine-rich linkers connecting to Aga2p and a c-myc tag for detection sterically accommodate receptor binding. While the receptors are heavily glycosylated, PDGF ligands are not, and therefore differences in glycosylation complexity between yeast and human are not anticipated to effect binding. This yeast display system is limited to studying interactions with homodimeric ligands, as co-expression of two ligands (e.g., PDGF-A and PDGF-B) will lead to a mixed population of all possible homo- and heterodimeric assemblies, making data interpretation challenging. This platform can likely be generalized to other related proteins due to high structural similarity amongst the family.

Figure 1B:
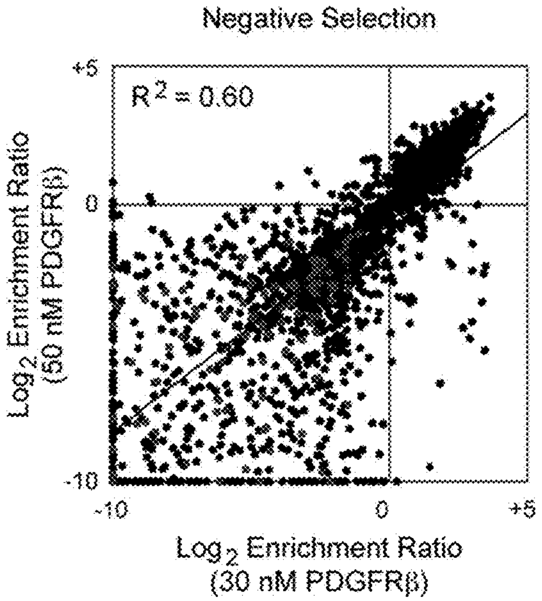
FIG. 1B is a correlation plot between duplicate sorting experiments showing log 2 enrichment ratios for each mutation after negative selection of PDGF-B variants that display low binding to PDGFRβ (bottom gate in FIG. 1A). Log 2 enrichment ratios show modest agreement between replicates.
Figure 1C:
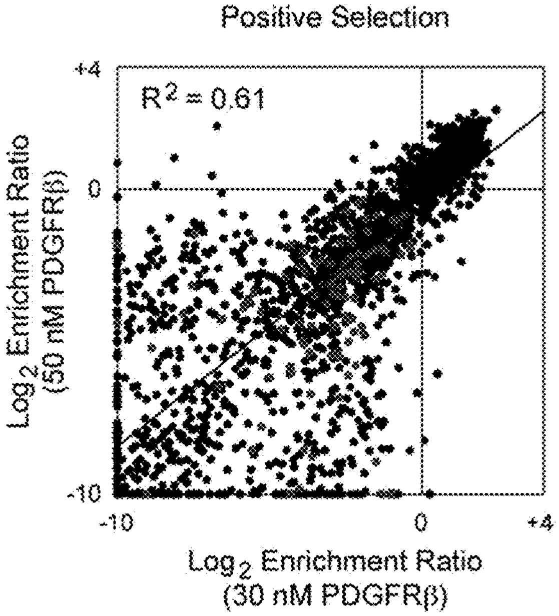
FIG. 1C is a correlation plot between duplicate sorting experiments showing log 2 enrichment ratios for each mutation after positive selection for PDGF-B variants that display high binding to PDGFRβ (top gate in FIG. 1A). Log 2 enrichment ratios show modest agreement between replicates.
Figure 1D:
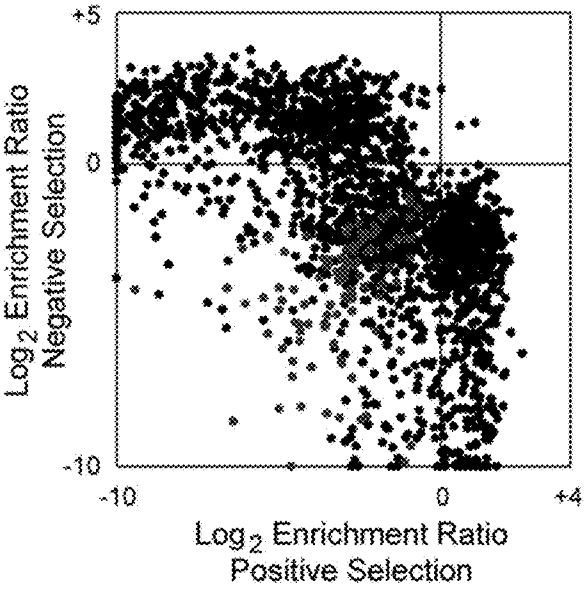
FIG. 1D is a correlation plot comparing mean log 2 enrichment ratios between negative and positive selections. As a generalization, mutations in the upper-left quadrant are deleterious for binding, in the lower-left quadrant are deleterious for expression, and in the lower-right quadrant are competent for PDGFRβ binding.

A yeast-displayed single site-saturation mutagenesis (SSM) library of PDGF-B was sorted by fluorescence-activated cell sorting (FACS) for high and low affinity interactions after incubating with fluorescently labeled PDGFRβ ectodomain (FIG. 1A). Mutants depleted in both sorted populations were poorly expressed (for instance, nonsense mutations were found in FIG. 1D), while mutants selectively enriched in the low binding population (upper-left quadrant in FIG. 1D) were expressed but had lost receptor association. The enrichment or depletion of all 2,080 single amino acid substitutions was tracked by deep sequencing, and the entire mutational landscape determined. Agreement between replicate experiments was high (FIG. 1B and FIG. 1C).

Figure 1E:
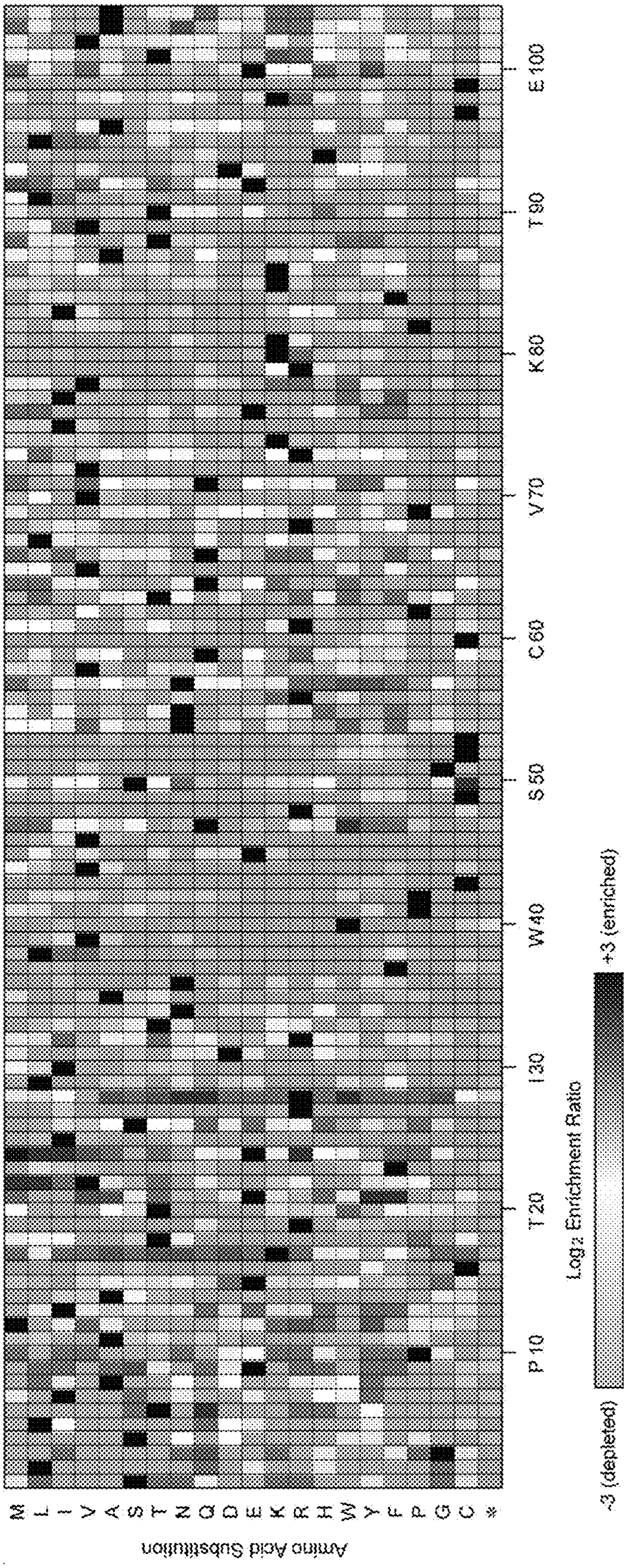
FIG. 1E is a heatmap showing the PDGF-B mutational landscape for high PDGFRβ binding (i.e. calculated from the enrichment of PDGF-B mutants expressed by yeast in the magenta collection gate in FIG. 1A). Log 2 enrichment ratios for all single amino acid substitutions (vertical axis) plotted across the PDGF-B sequence (horizontal axis), with deleterious mutations lighter, neutral in white, and gain-of-function mutations darker. * indicates stop codons. Wild type amino acids are black.
Figure 2:
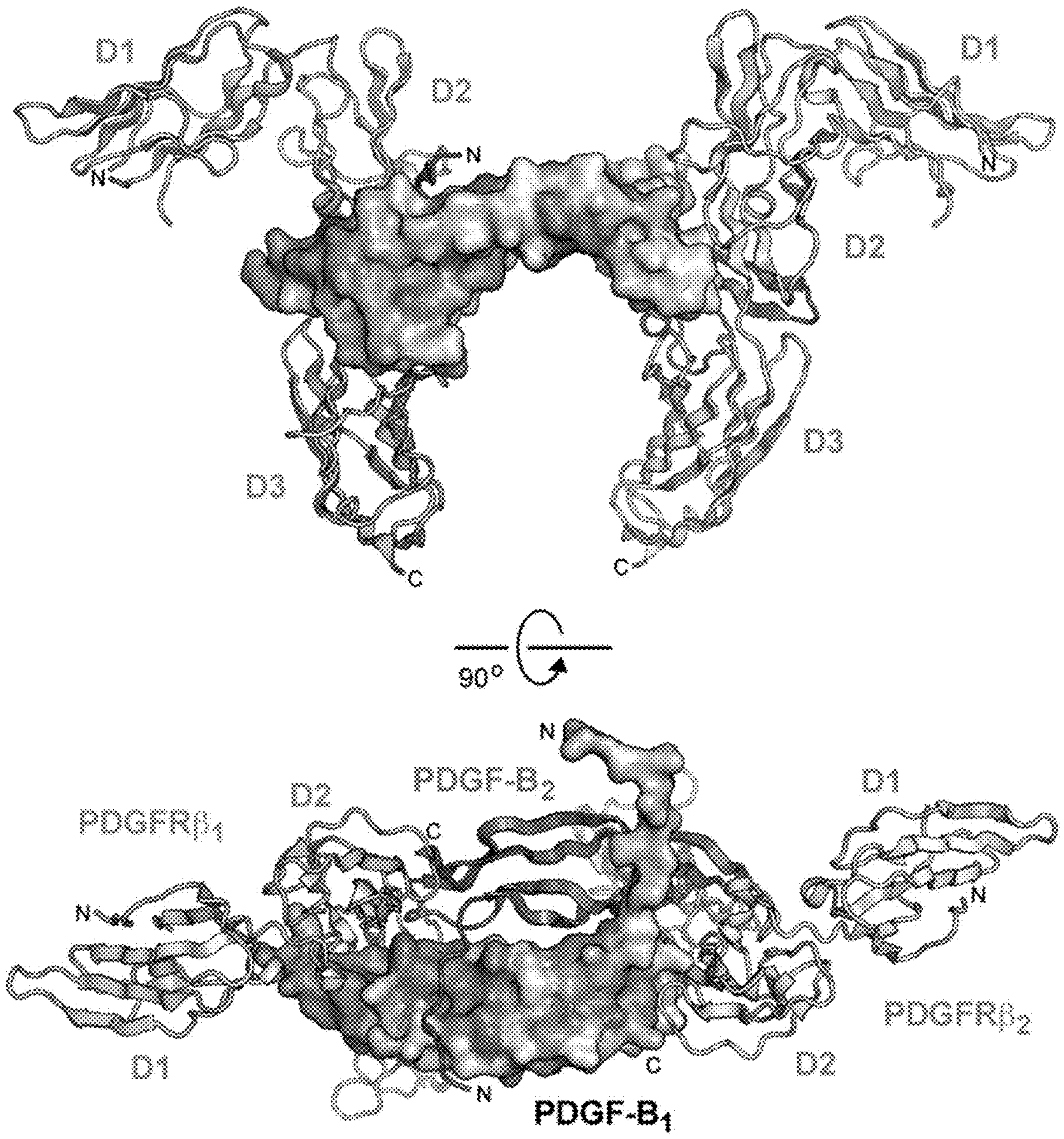
FIG. 2 shows conservation scores from the PDGF-B mutational scan mapped to the surface of a single ligand subunit in the PDGF-BB-PDGFRβ crystal structure (PDB: 3MJG), from conserved, to mutationally tolerant, to residues under selection for change. Receptor chains and the second ligand chain are also shown. Interacting residues of the protruding ligand (PDGF-Bi binding to PDGFR$\beta_1$) are less tolerant of mutation than interacting residues of the receding ligand (PDGF-Bi binding to PDGFR$\beta_2$)
Figure 3A:
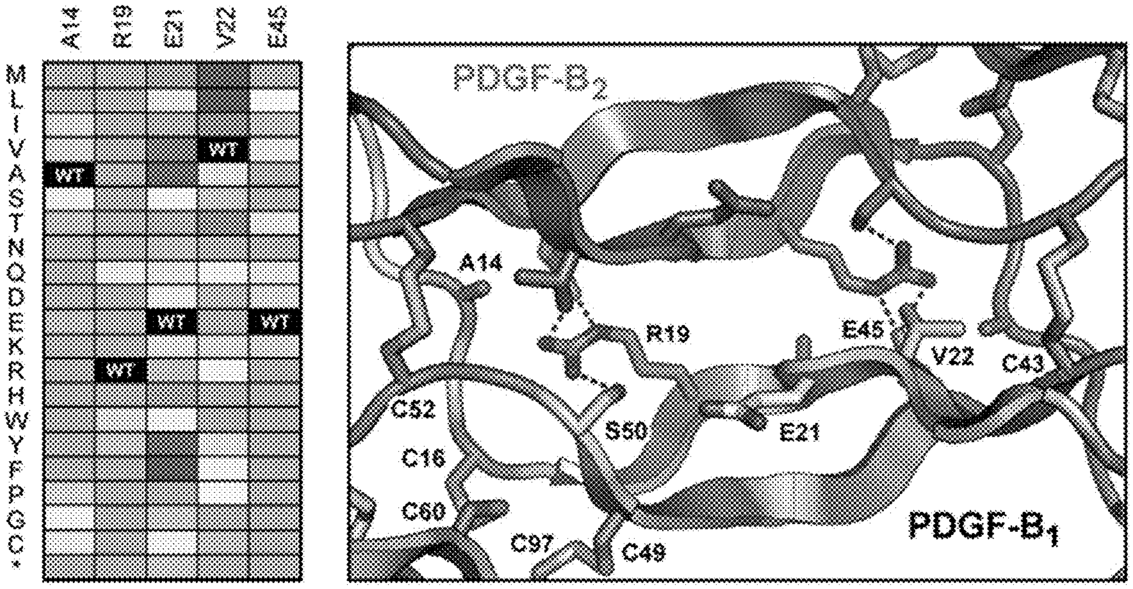
FIG. 3A is a representative close up view of the PDGF-BB dimer interface in the PDGF-BB-PDGFRβ crystal structure (PDB:3MJG). One PDGF-B subunit is colored from high conservation to neutral to under selection for change based on the positive selection for PDGFRβ binding. The second PDGF-B subunit and PDGFRβ chains are also shown. Heatmap on the left shows the log 2 enrichment ratios of single PDGF-B substitutions for PDGFRβ binding, from deleterious/depleted (light) to enriched (dark). Wild type (WT) amino acids are black.
Figure 3B:
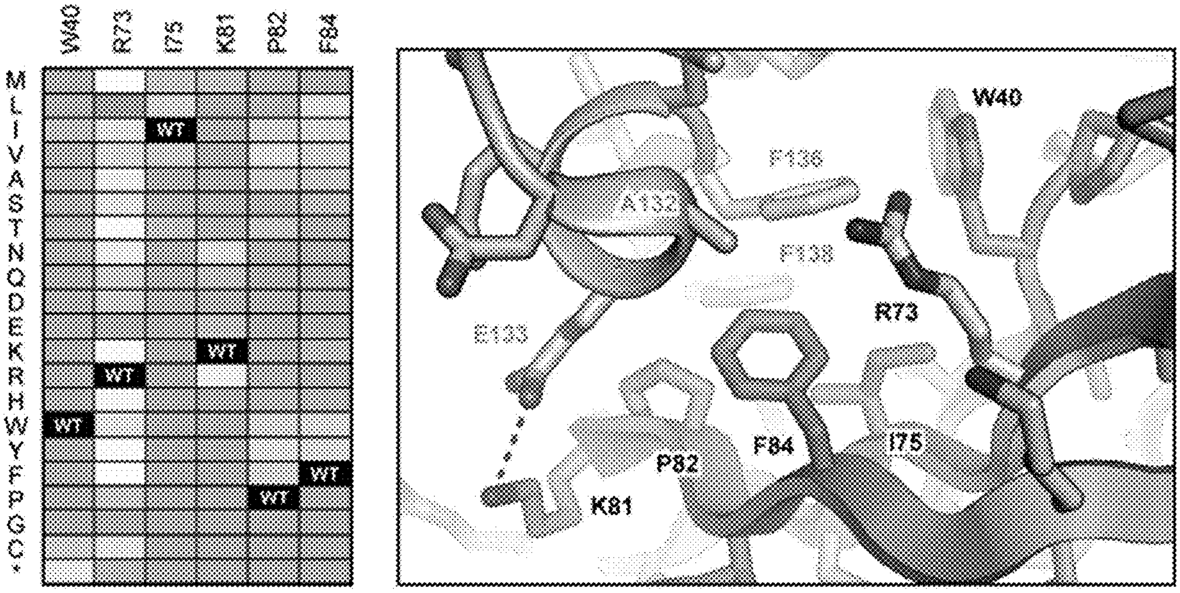
FIG. 3B is a representative close up view of the PDGF-BB-PDGFRβ crystal structure (PDB:3MJG) showing interactions by the protruding PDGF-B subunit. The PDGF-B subunit is colored from high conservation to neutral to under selection for change based on the positive selection for PDGFRβ binding. Heatmap on the left shows the log 2 enrichment ratios of single PDGF-B substitutions for PDGFRβ binding, from deleterious/depleted (light) to enriched (dark). Wild type (WT) amino acids are black.
Figure 3C:
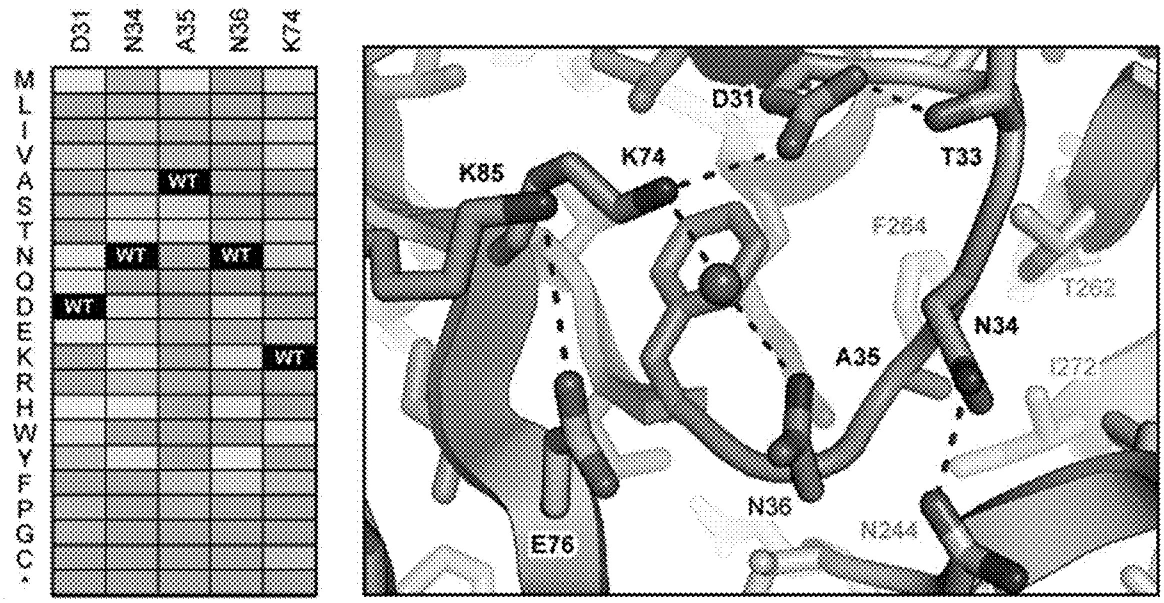
FIG. 3C is a representative close up view of the PDGF-BB-PDGFRβ crystal structure (PDB:3MJG) showing interactions by the protruding PDGF-B subunit. PDGF-B is colored from high conservation to neutral to under selection for change based on the positive selection for PDGFRβ binding. PDGFRβ is also shown. Heatmap on the left shows show the log 2 enrichment ratios of single PDGF-B substitutions for PDGFRβ binding, from deleterious/depleted (light) to enriched (dark). Wild type (WT) amino acids are black.
Figure 3D:
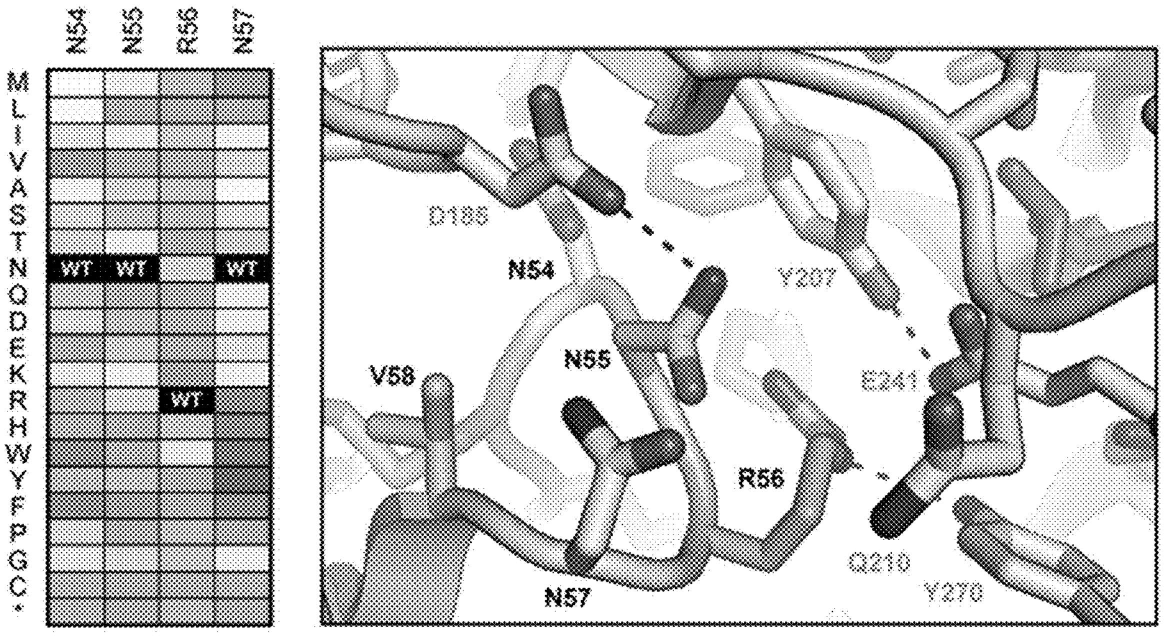
FIG. 3D is a representative close up view of the PDGF-BB-PDGFRβ crystal structure (PDB:3MJG) showing interactions by the receding PDGF-B subunit. The receding PDGF-B subunit is colored from high conservation to neutral to under selection for change based on the positive selection for PDGFRβ binding. The protruding PDGF-B subunit and PDGFRβ is are also shown. Heatmap on the left shows the log 2 enrichment ratios of single PDGF-B substitutions for PDGFRβ binding, from deleterious/depleted (light) to enriched (dark). Wild type (WT) amino acids are black.

From the mutational landscape (FIG. 1E and FIG. 2), it was observed that all cysteine residues forming three intra- and two interchain disulfides were highly conserved, indicating that PDGF-B was correctly folded into disulfide-linked dimers on the yeast surface. Indeed, several mutations at the ligand dimer interface were found that were enriched and might have enhanced dimerization through increased hydrophobic packing (e.g. V22L) or reduced electrostatic repulsion (e.g. E21Y) (FIG. 3A). The mutational scan therefore informed how sequence dictates ligand-ligand association, in addition to ligand-receptor interactions. Further, residues from the protruding PDGF-B subunit in contact with the receptor (PDGF-Bi and PDGFR$\beta_1$ subunits in FIG. 2) were tightly conserved (FIG. 3B and FIG. 3C), whereas interfacial residues from the receding ligand (PDGF-Bi and PDGFRβ2 subunits in FIG. 2) were more mutationally tolerant (FIG. 3D).

Figure 4A:
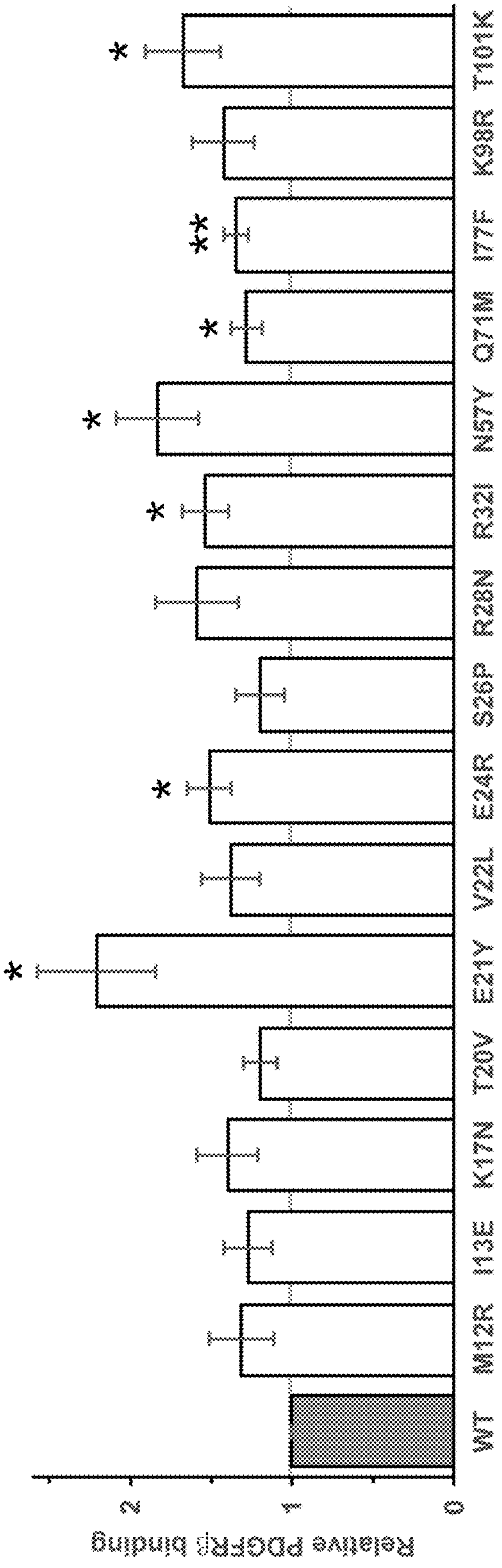
FIG. 4A is a bar graph showing binding of the PDGFRβ extracellular domain to wild type (WT) and mutant PDGF-B displayed on the yeast surface, measured by flow cytometry. Yeast were gated for equivalent levels of PDGF-B surface expression. * $p<0.05$, ** $p<0.01$, Student's t test. Data are average of ΔMean Fluorescence Units (MFU)±SD, n=5.
Figure 4B:
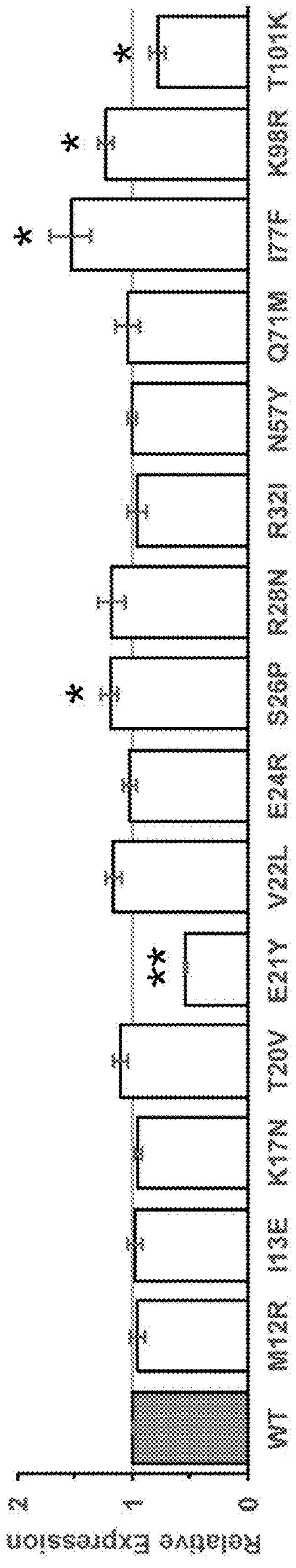
FIG. 4B is a bar graph showing expression of PDGF-B mutants on the yeast surface relative to WT. Data are average of ΔMFU±SD, n=6.

There were enriched mutations at the receptor interface that the scan predicted increased PDGF-BB-PDGFRβ affinity, and these were further explored by targeted mutagenesis. Fifteen mutations at the receptor and ligand interfaces were tested by yeast surface display, and all trended towards higher binding signal after gating for equivalent expression (FIG. 4A), with seven showing statistical significance ($p<0.05$, Student's t-test). Most of the mutations caused only minor changes in expression on the yeast surface (FIG. 4B). 11 mutations were chosen for inclusion in a small yeast-displayed combinatorial library of 2,048 possible variants, which was enriched by FACS for high binding signal to the ectodomain of PDGFRβ. 8 individual clones with elevated binding were sequenced, representing 7 unique PDGF-B variants (FIG. 5A). The full PDGF-B sequence of the 8 clones is provided in Table 1 above, along with a consensus sequence (PDGF-B-cons) containing the most common mutations (SEQ ID NOs: 2-9).

Figure 6A:
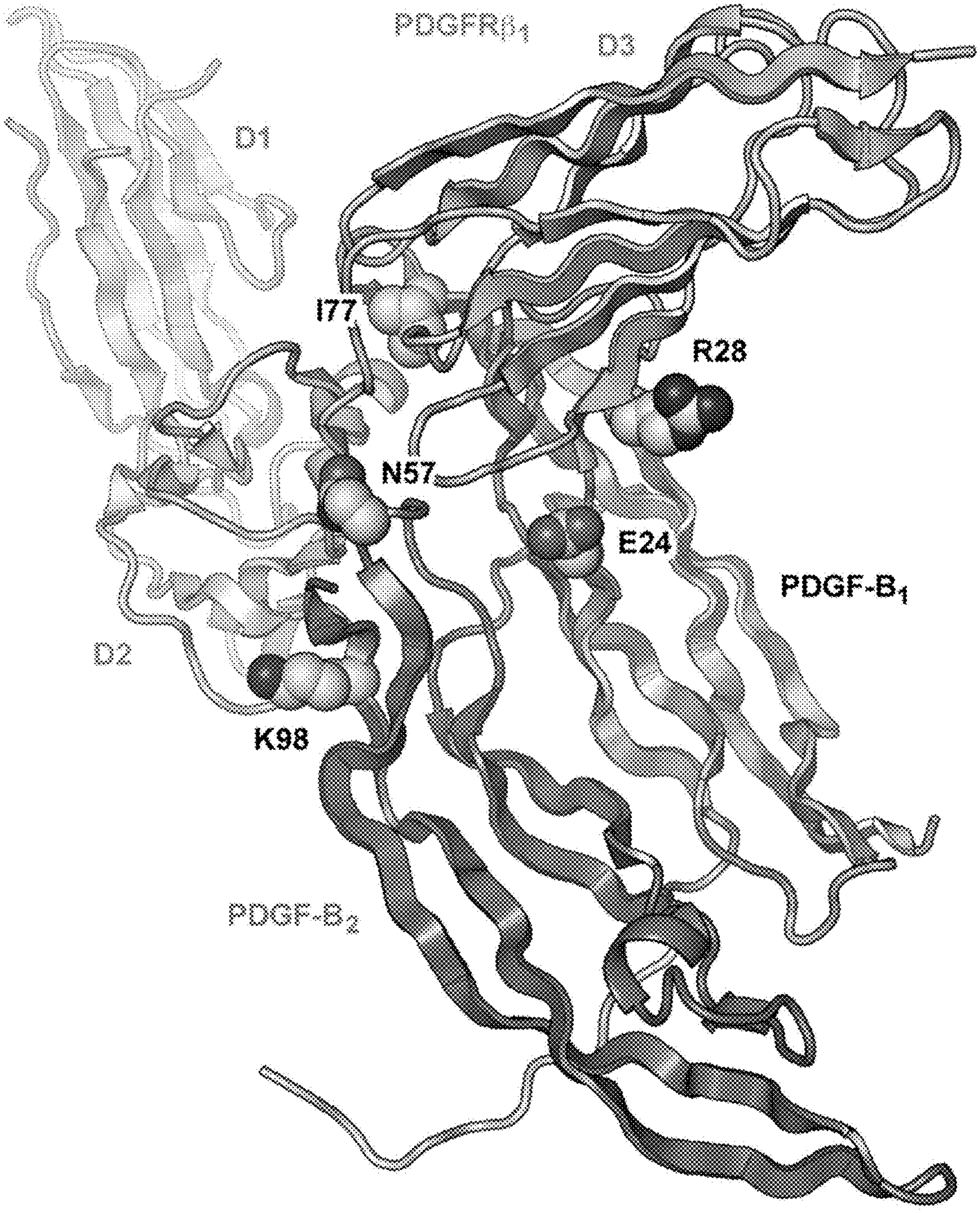
FIG. 6A shows the structure of PDGFRβ interacting with the PDGF-BB dimer. Residues of PDGF-BB (protruding subunit colored by high conservation to low conservation; receding subunit is grey) that are substituted in PDGF-BB-cons are highlighted with light spheres on the crystal structure (PDB: 3MJG). A single bound receptor chain is also shown.
Figure 6B:
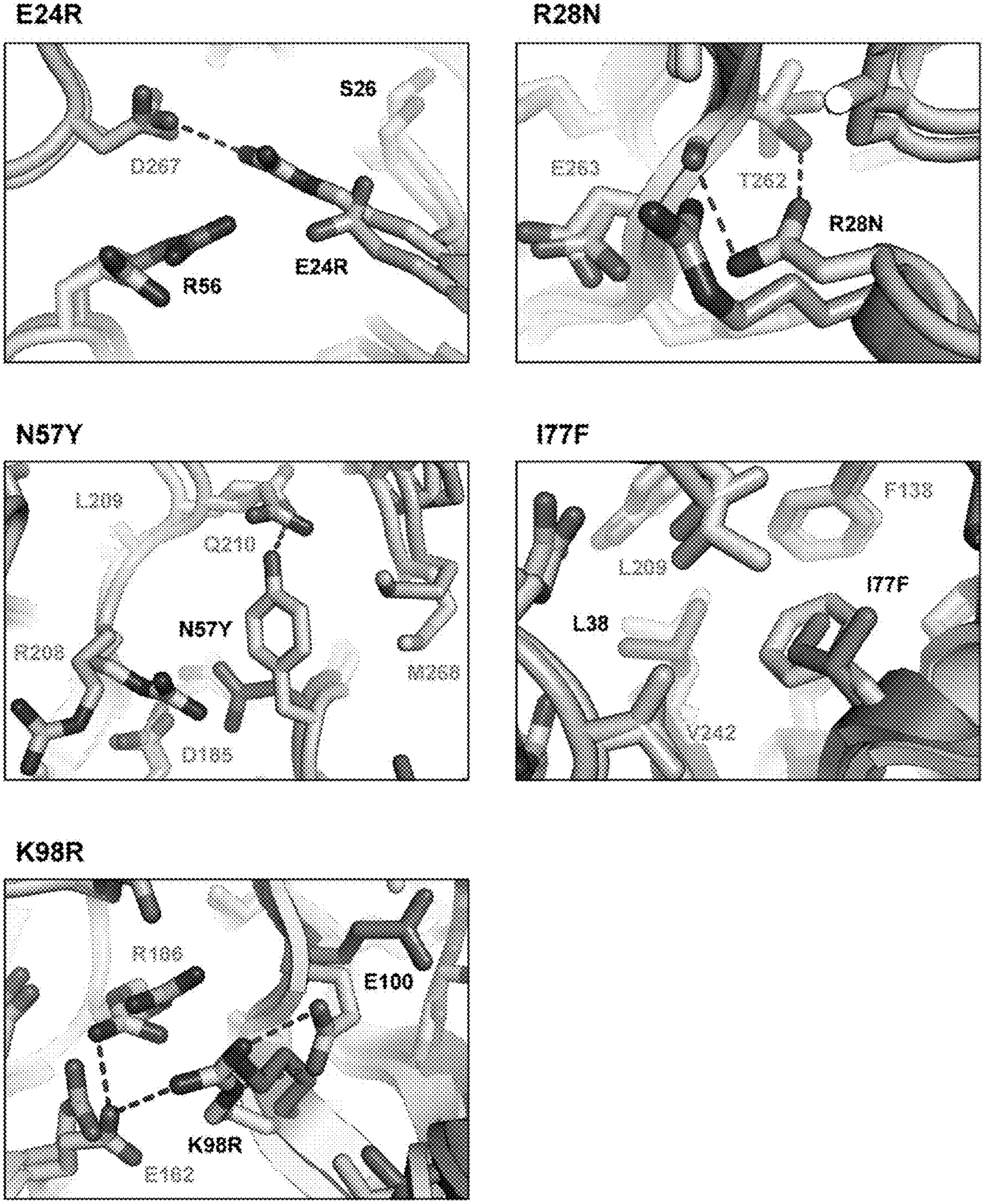
FIG. 6B shows PDGF-BB-cons bound to PDGFRβ as modeled using ROSETTA. The model is aligned to the crystal structure colored as in FIG. 6A. Regions of PDGF-BB-cons mutations are shown.

When expressed on the yeast surface, the consensus sequence of the isolated clones had equivalent binding to soluble PDGFRβ as two identical clones with exceptional properties (clones-04 and 05, which were renamed PDGF-B-hi; SEQ ID NO: 5; FIG. 5A and FIG. 5B). The consensus sequence, from here-on-in referred to as PDGF-B-cons (SEQ ID NO: 9), was also highly expressed (FIG. 5C), suggesting it was likely amenable to purification and characterization in solution. PDGF-B-cons had five amino acid substitutions that were dispersed and spatially segregated across the entire interface (FIG. 6A), which likely facilitated their combination without deleterious epistasis. Three of the mutations were at the PDGFRβ interaction surface with the protruding PDGF-B subunit (FIG. 6B): PDGF-B-E24R increased electropositive charge for interaction with PDGFRβ-D267, PDGF-B-R28N was predicted to create new hydrogen bonds to an edge strand of PDGFRβ domain D3, and PDGF-B-I77F increased hydrophobic packing within a pocket at the PDGFRβ D2-D3 junction. The remaining two substitutions in the consensus sequence were at the PDGFRβ interface with the receding PDGF-B subunit (FIG. 6B): PDGF-B-N57Y likely increased apolar contacts at the PDGFRβ D2-D3 junction, and the conservative PDGF-B-K98R mutation might have allowed hydrogen bonding to PDGFRβ-E162.

Example 2: VEGF and PDGF: Exploring Canonical and Non-Canonical Binding and Signaling Angiogenesis is a key pathogenic component of at least 70 known diseases, including: diabetes, Crohn's disease, and obesity. It is primarily driven by the vascular endothelial growth factor receptor (VEGFR) and its family of VEGF ligands. However, targeting VEGF alone has not achieved the promise of stable vascular control. This is because angiogenesis involves several signaling axes, in addition to VEGF, representing a complexity that cannot be captured by targeting one growth factor alone. There is a need to shift the pedagogy away from a uni-axis understanding of vascularization (e.g. VEGF alone) towards a multi-axis understanding (e.g., VEGF+PDGF, etc.).

An experimental and computational systems biology framework was applied to examine cross-family signaling in receptor regulation, wherein ligands from one growth factor family bind to and signal through receptor(s) of another family.

Figure 7:
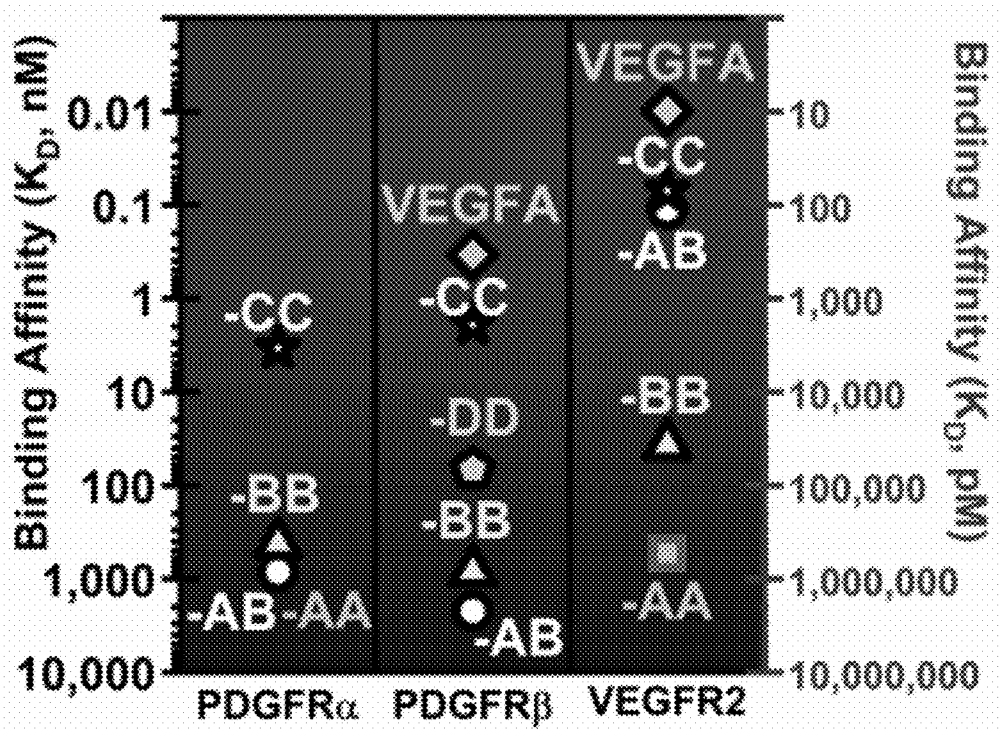
FIG. 7 shows PDGFRα (left), PDGFRβ (center), and VEGFR2 (right) binding affinity measurements for VEGFA and PDGF dimers AA, AB, BB, and CC.

The cross-family binding affinities of recombinant PDGFs:VEGFR2 were measured via surface plasmon resonance. The measurements revealed high-affinity binding between PDGFs and VEGFR2 (FIG. 7). Indeed, PDGFs-AB, -BB, and -CC had a higher binding affinity to VEGFR2 than they did to their canonical PDGFR binding partners.

The following is a sensitivity analysis of VEGFR interactions. Deterministic computational models of cross-family PDGF:VEGFR2 binding were constructed and simulated using MATLAB SimBiology. The computational models identified several physiological conditions where PDGF:VEGFR2 binding interactions could dominate, including conditions of high VEGFR2 concentrations on the plasma membrane and when PDGF degradation was inhibited (FIG. 8).

Figure 8:
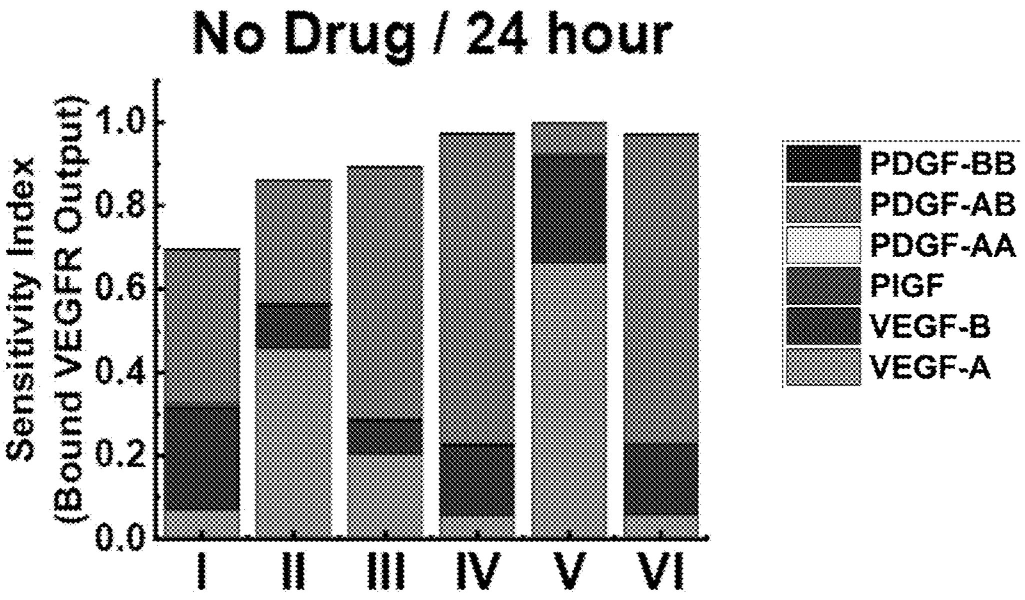
FIG. 8 shows a sensitivity analysis of VEGFR interactions. It depicts a global sensitivity computational analysis of cross-family (PDGF vs. VEGF) signaling. Each column describes a different model described more fully below, and the legend labels different ligands by color.

The significance of PDGF:VEGFR2 cross-family interactions was explored in relation to canonical VEGFR interactions under six biological conditions using a global sensitivity analysis (FIG. 8). These conditions included disruption of ligand-mediated receptor internalization (Model I vs II), receptor overexpression (II vs III), a receptor recycling condition that maintains a steady state concentration of VEGFRs on the plasma membrane (I vs IV), pharmacokinetic clearance of ligands (IV vs V), and ligand secretion to balance clearance (V vs VI).

Model I was the base model, which represented a healthy condition and was constructed by recapitulating the model from (Mamer et al., *Sci Rep* 7, 16439 (2017)) with four key additions: (1) inclusion of PlGF:VEGFR1 interactions; (2) inclusion of VEGF-B:VEGFR1 interactions; (3) updating receptor trafficking rates to reflect that of HUVECs; and (4) updating ligand concentrations to a current understanding of healthy human serum values. Parameterization was performed using HUVEC data because they are a standard and well characterized in-vitro model for angiogenic activity, whereas prior trafficking rates reflected a cell-type that is presumed to have differential trafficking due to its very high VEGFR expression compared to HUVECs (human colon microvascular endothelial cells).

Each model helped with understanding how disease characteristics affect ligation. This was done by starting with the aforementioned base model (Model I) and incorporating one change at a time to each model. A key branch-point was going from Model I to either Model II or Model IV. Model II examined how changes in receptor internalization affect ligation, while Model IV examined how changes in receptor recycling affect ligation. To begin, the internalization transition from Model I to Model II and from Model II to Model III is described. Then, the recycling transition from Model I to Model IV and from Model IV to Model V and VI is described.

As described above, the Model I to Model II transition compared how disrupting ligand-mediated internalization (e.g., disrupting clathrin mediated endocytosis) affects occupancy. Internalization disruptions have been observed in several diseases, including: cancer, type A-B Niemann-Pick disease, and FCH domain only 1 deficiency. This disruption in ligand-mediated internalization was added into Model II by eliminating the fast, ligand-mediated receptor internalization that is present in Model I. This change in Model II allowed all receptor and receptor:ligand complex internalizations to happen at the same rate.

Model III built upon Model II by adding receptor overexpression, which is characteristic of several cancers. Receptor overexpression was added to Model III by increasing the receptor insertion rate by an order-of-magnitude.

The transition from Model I to Model IV explored how receptor recycling affects ligation. This exploration is relevant to the pathologies of cancer and Huntington's disease. The change in recycling that occurred in Model IV was performed by setting receptor recycling rates equal to receptor internalization rates, which kept total receptor concentrations constant through the simulation. Insertion can be pathologically affected through disruption of the RAB4 and RAB11 pathways.

Model V built upon Model IV by incorporating growth factor clearance. Model VI built upon Model V by incorporating growth factor secretion to balance the clearance rate.

Under short time (1 hour) sensitivity analyses, the different models were similar and showed that PDGF-AB had strong control over VEGFR2 occupancy with the exception of model V where protein degradation was introduced. When the signaling response was integrated over 24 hours, more significant differences were seen between the models. For instance, PDGF-AB was a stronger controller of VEGFR2 ligation in Model IV when there were constant receptors on the surface, compared with Model II where the internalization rates were the same for receptors-ligated and unligated receptors. Overall, the simulations showed that PDGF-AB had a strong capacity to control VEGFR2 occupancy across several physiological states.

These experiments showed that significant PDGF binding and signaling could occur via VEGFR2, providing support for the use of PDGF variants to modulate VEGFR signaling.

Example 3: Cell Culture Methods hTERT-immortalized Dermal Microvascular Endothelial Cells (HDMECs) (ATCC, Cat. #CRL-4060) were gene-edited for a PDGFRα/β double knockout line (Washington University in St. Louis, Genome Engineering and iPSC Center) that was used for all experiments in this study. The gene-edited hTERT-immortalized human dermal microvascular endothelial cells (HDMECs) and human dermal fibroblasts (HDFs) were maintained under sterile conditions in tissue-culture treated T-75 flasks at 37° C. and 5% C02 during normal culture and experiments, and they were passaged up to 6 times before experiments. Media for both cell types were changed every other day, and both cell types were passaged at 70% confluence. HDMECs were grown in Vascular Cell Basal Medium (ATCC, Cat. #PCS-100-030) supplemented with Microvascular Endothelial Cell Growth Kit-VEGF (ATCC, Cat. #PCS-110-041). HDFs were grown in DMEM with high glucose and sodium pyruvate (Cat. #11995-065)+10% FBS.

Canonical VEGFR/PDGFR ligands such as VEGF-A (R&D Systems, Cat. #293VE050CF), PDGF-AA (R&D Systems, Cat. #221-AA-050), PDGF-AB (R&D Systems, Cat. #222-AB-050), PDGF-BB (R&D Systems, Cat. #220-BB-050), PDGF-CC (R&D Systems, Cat. #1687CC025CF), and PDGF-DD (R&D Systems, Cat. #1159-SB-025/CF) were used during experiments as well as PDGF-BB mutants manufactured by Bon Opus Biosciences in an E. Co/i expression system. Mutant PDGF-B ligands A-F used were those described in Table 1 above.

Example 4: Scratch Assays after Ligand Stimulation

PDGF-BB is currently used for wound healing, and a PDGF-BB mutant could be identified that results in better wound healing. A scratch assay was performed to identify such a mutant.

Figure 9:
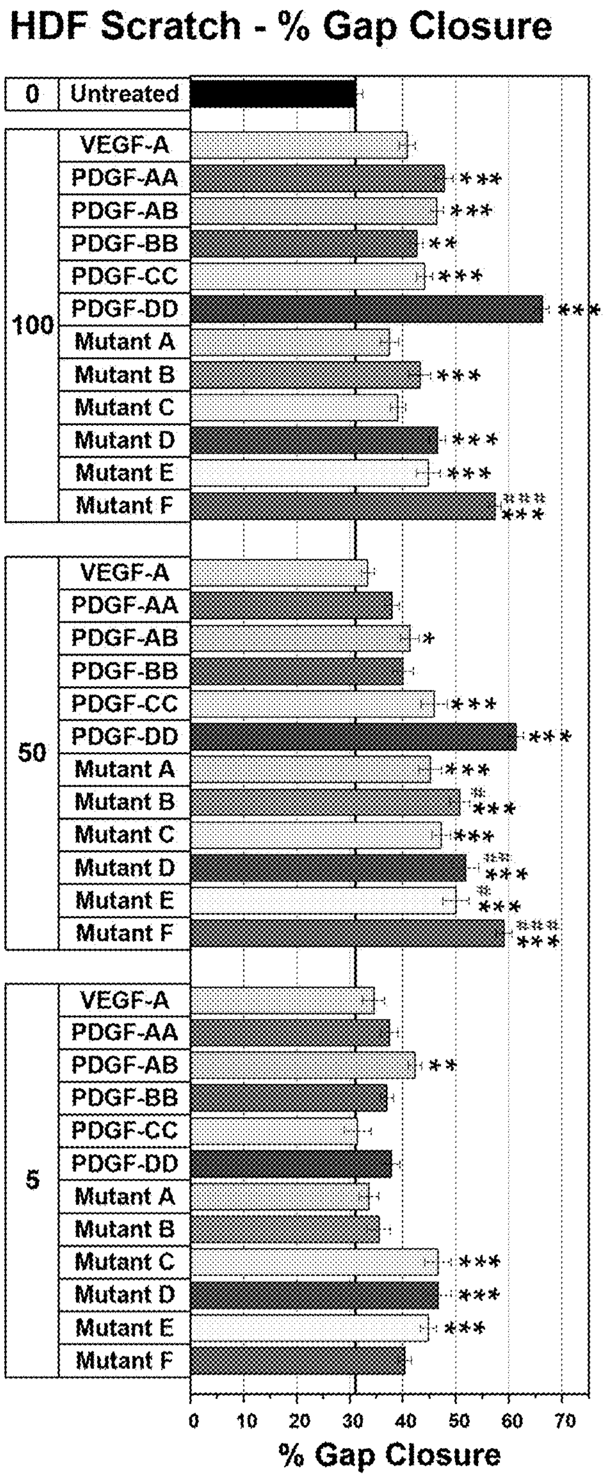
FIG. 9 depicts a human dermal fibroblast (HDF) scratch assay measuring percent gap closure after ligand stimulation. HDF migration was measured using wound-healing assays at 0 and 24 hours post scratch. Wound area was measured using ImageJ, and the percent gap closure was calculated. Significance was determined using a one-way ANOVA, and pairwise comparisons were made using the Tukey Test. * indicates a value significantly different than the untreated condition. # indicates a mutant significantly different from PDGF-BB at the same concentration. * or # indicates $p<0.05$.  or ## indicates $p<0.01$. * or ### indicates $p<0.001$. N=20.
Figure 12:
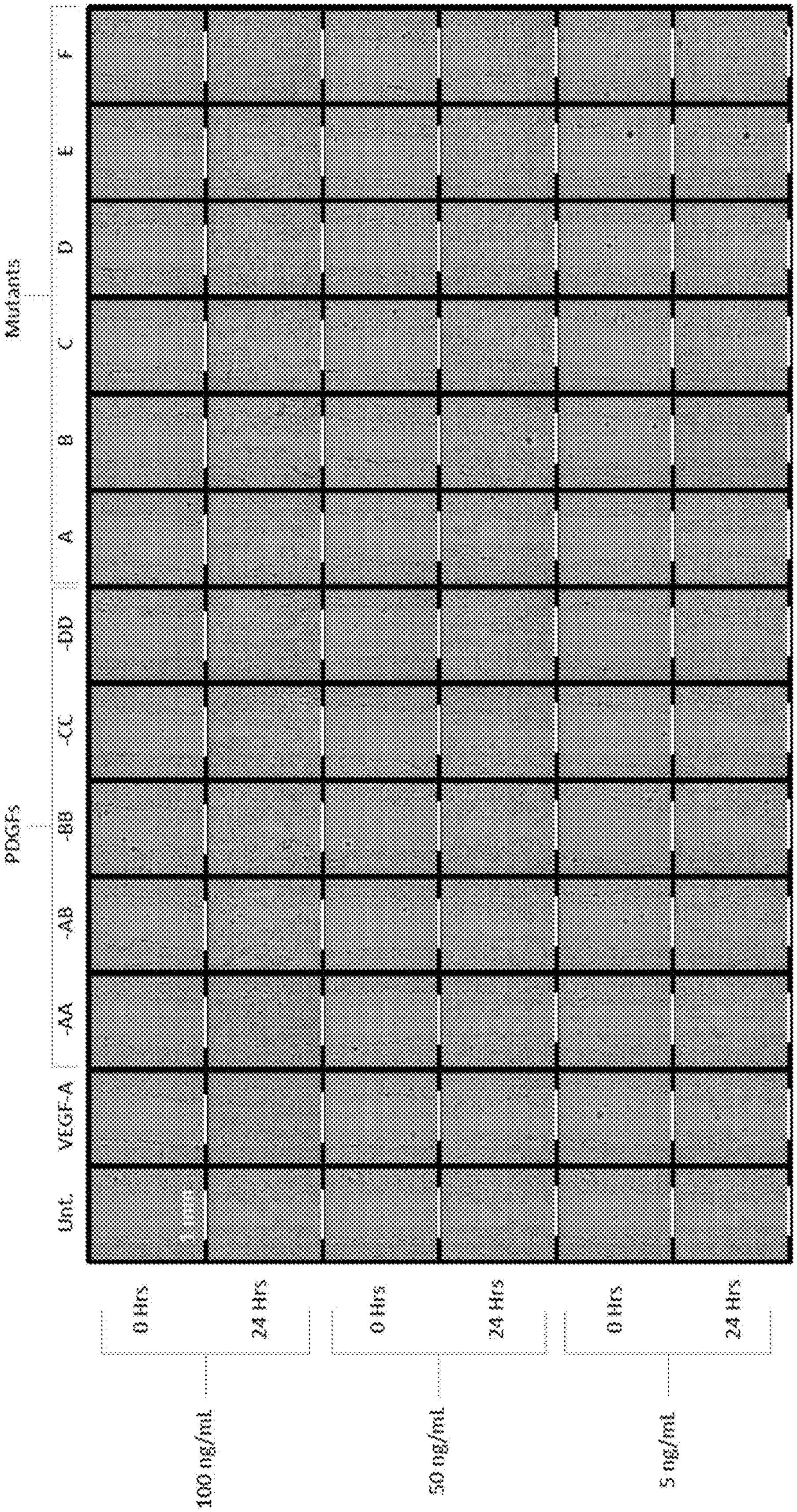
FIG. 12 depicts representative scratches from the PDGFRα/β double knockout human dermal microvascular endothelial cell scratch assay quantified in FIG. 11.

To measure the effect of PDGFs on VEGFR+/PDGFR− endothelial cell and VEGFR−/PDGFR+HDF migration, a high-throughput, quantitative wound healing assay was used. Cells were seeded in 24-well plates (marked on the bottom with a marker for imaging precision) and grown to 95% confluence. Cells were then starved for 3 hours before the monolayer was scratched with a p200 pipette tip. Starvation/treatment media for HDMECs consisted of Vascular Cell Basal Medium, 1% FBS, L-glutamine, heparin sulfate, hydrocortisone, and ascorbic acid. Starvation/treatment media for HDFs consisted of DMEM with high glucose and sodium pyruvate+1% FBS. After the scratch was made, wells were rinsed with starvation media once to remove debris before treatments were added. Cells were treated with VEGF-A, PDGF-AA, PDGF-BB, PDGF-CC, PDGF-DD, and PDGF-BB mutants A-F (SEQ ID NOs: 2, 5, 12, 4, 10, and 11, respectively) at varying concentrations (5, 50, and 100 ng/mL). Images of the wound were taken on an EVOS m5000 microscope immediately after treatments were added, and once more 24 to 50 hours later. The images were processed, and wound areas were measured using ImageJ. A power analysis was performed to ensure a sufficient sample size; $p<0.05$ using ANOVA/Tukey with $20<n<22$. Quantification is shown in FIG. 9 for HDF cells with representative stills shown in FIG. 10. Quantification is shown in FIG. 11 for HDMEC cells with representative stills shown in FIG. 12.

For the HDF cells in FIG. 9, at the lowest dose tested (5 ng/mL), no mutant had higher gap closure than PDGF-BB, but three mutants (C, D, E) had a higher gap closure than the untreated condition. Four mutants (B, D, E, F) showed significantly greater wound healing over PDGF-BB at 50 ng/mL dose. Mutant F resulted in significantly higher wound healing over both untreated and PDGF-BB treated fibroblasts at 50 and 100 ng/mL treatment. Overall, every mutant had a dose offering greater wound healing compared to untreated. Four mutants (B, D, E, and F) had at least one dose surpassing PDGF-BB treatment.

Figure 10:
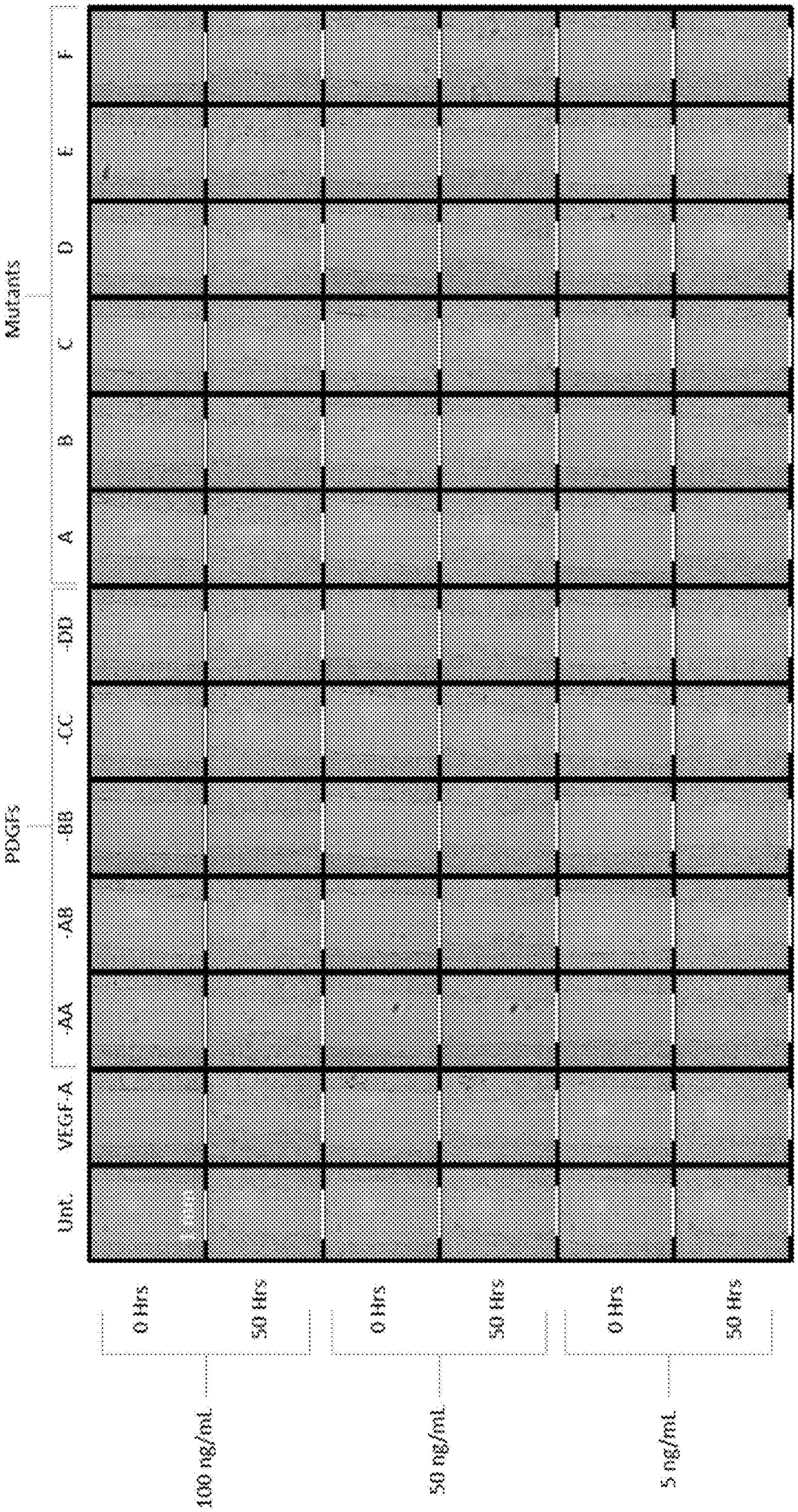
FIG. 10 depicts representative scratches from the human dermal fibroblast scratch assay quantified in FIG. 9.

For the HDMEC cells in FIG. 10, at the highest dose tested (100 ng/mL), no mutant had higher gap closure than PDGF-BB, but three mutants (A, C, and D) had higher gap closure than the untreated condition.

These results indicate a PDGF-B mutant could be used for improved wound healing.

Example 5: Proliferation Assays after Ligand Stimulation

To determine PDGFs' effects on EC and HDF proliferation, a sulforhodamine B (Sigma-Aldrich, Cat. #230162) assay (a colorimetric proliferation assay) was used that uses protein content to measure cell densities. First, cells were seeded at approximately 50% confluence in 96-well plates with 50 μL starvation media/well. The cells were allowed to attach to the plate for 5 hours before 50 μL of 2× concentrated treatment media was added to each well. Immediately after treatment, an untreated control plate was collected and the cells were fixed with trichloroacetic acid (Sigma-Aldrich, Cat. #91228). After 24 hours, the remaining assay plates were fixed with trichloroacetic acid. For the fixation procedure, an equal volume of ice-cold 20% trichloroacetic acid (w/v) was added directly to the media of each well to fix the cells, which were incubated at 4° C. for 1 hour before being rinsed twice with DI water. Fixed wells were then incubated with 50 μL of 0.057% SRB (w/v) in 1% acetic acid for 30 minutes before being rinsed with 1% acetic acid. The SRB contained in the fixed cells was then solubilized with 200 μL of 10 mM unbuffered Tris base solution and read (ex/em, 488 nm/585 nm) on a plate reader (Perkin Elmer EnSpire 2300 Multilabel Multimode Plate Reader).

Figure 13:
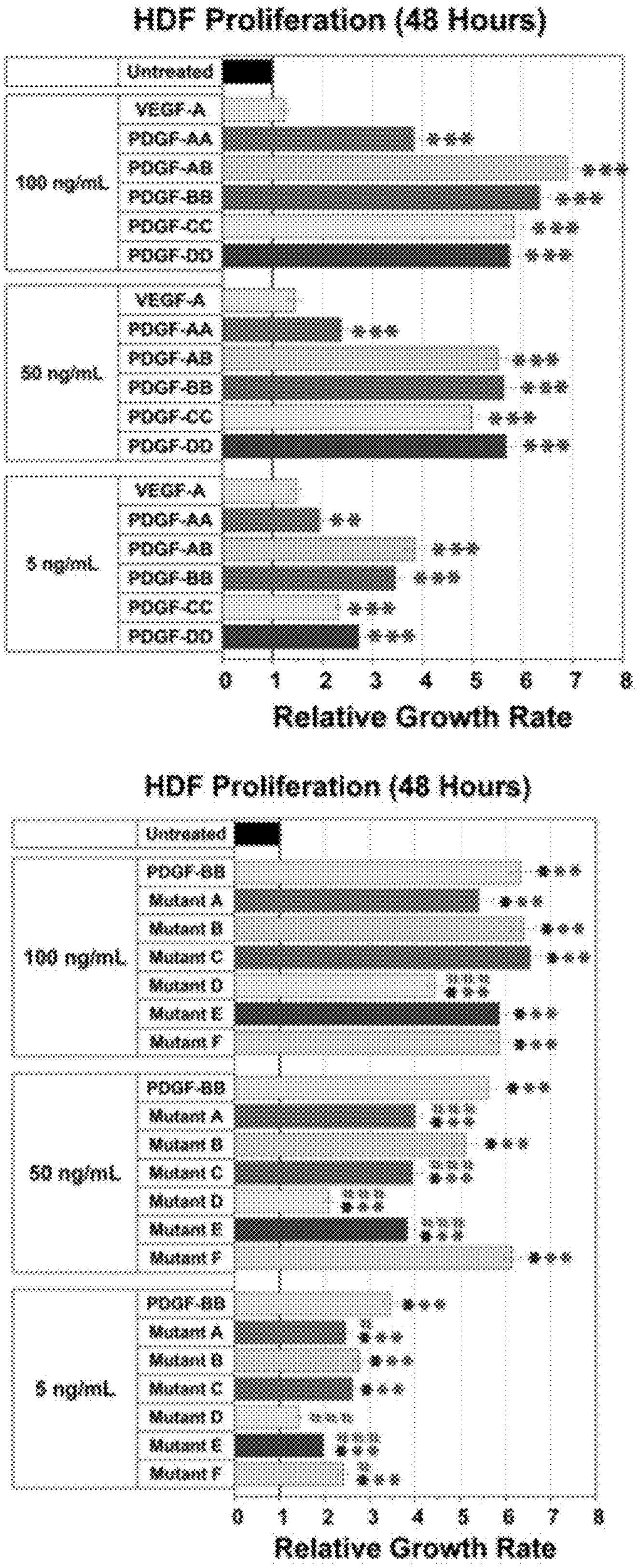
FIG. 13 depicts a human dermal fibroblast (HDF) proliferation assay measuring relative growth rate at 48 hours after ligand stimulation. Relative growth rate was measured using a sulforhodamine colorimetric proliferation assay that uses protein content to measure cell densities. * indicates a value significantly different than the untreated condition. # indicates a mutant significantly different from PDGF-BB at the same concentration. * or # indicates $p<0.05$.  or ## indicates $p<0.01$. * or ### indicates $p<0.001$.

For HDF cells in FIG. 13, cells treated with 50 ng/mL or 100 ng/mL of mutants A-F had an increased growth rate compared to untreated cells. Cells treated with 100 ng/mL of mutants A, B, C, E, or F had relative growth rates that were not significantly different from treatment with PDGF-BB.

Figure 14:
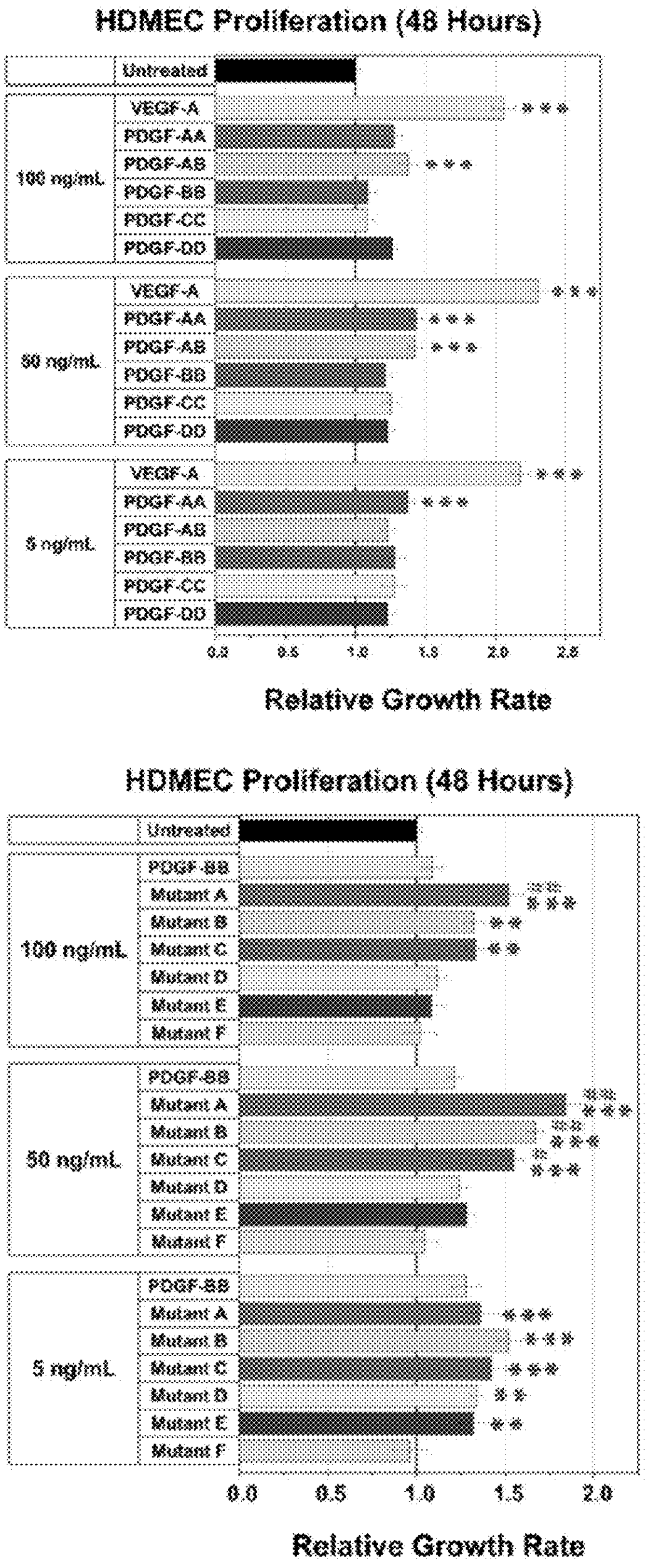
FIG. 14 depicts a PDGFRα/β double knockout human dermal microvascular endothelial cell (HDMEC) proliferation assay measuring relative growth rate at 48 hours after ligand stimulation. Relative growth rate was measured using a sulforhodamine colorimetric proliferation assay that uses protein content to measure cell densities. * indicates a value significantly different than the untreated condition. # indicates a mutant significantly different from PDGF-BB at the same concentration. * or # indicates $p<0.05$.  or ## indicates $p<0.01$. * or ### indicates $p<0.001$.

For HDMEC cells in FIG. 14, cells treated with 5 ng/mL of mutants A-E had an increased growth rate compared to untreated cells. None of mutants A-F at 5 ng/mL were significantly different from treatment with PDGF-BB.

These results indicate wild type or mutant PDGF-B can be used for increased cell proliferation.

Example 6: Enzyme-Linked Immunosorbent Assay (ELISA) Measuring PDGFR Phosphorylation after Ligand Stimulation Total PDGFR phosphorylation after ligand stimulation was determined using ELISA kits for each receptor (R&D Systems, Cat. #s DYC2114 and DYC1767). For sample preparation, HDFs were grown to confluence in 6-well plates, incubated for 3 hours with serum-free DMEM, and then treated with individual ligands for 10 minutes before samples were lysed with the supplied lysis buffer reagent. The protocols and materials supplied in each kit were followed and used, respectively, to carry out this experiment in a 96 well plate format. Provided standards were assayed alongside samples as a positive control. Absorbance readouts were measured on a plate reader at 450 nm (Perkin Elmer EnSpire 2300 Multilabel Multimode Plate Reader).

Figure 15A:
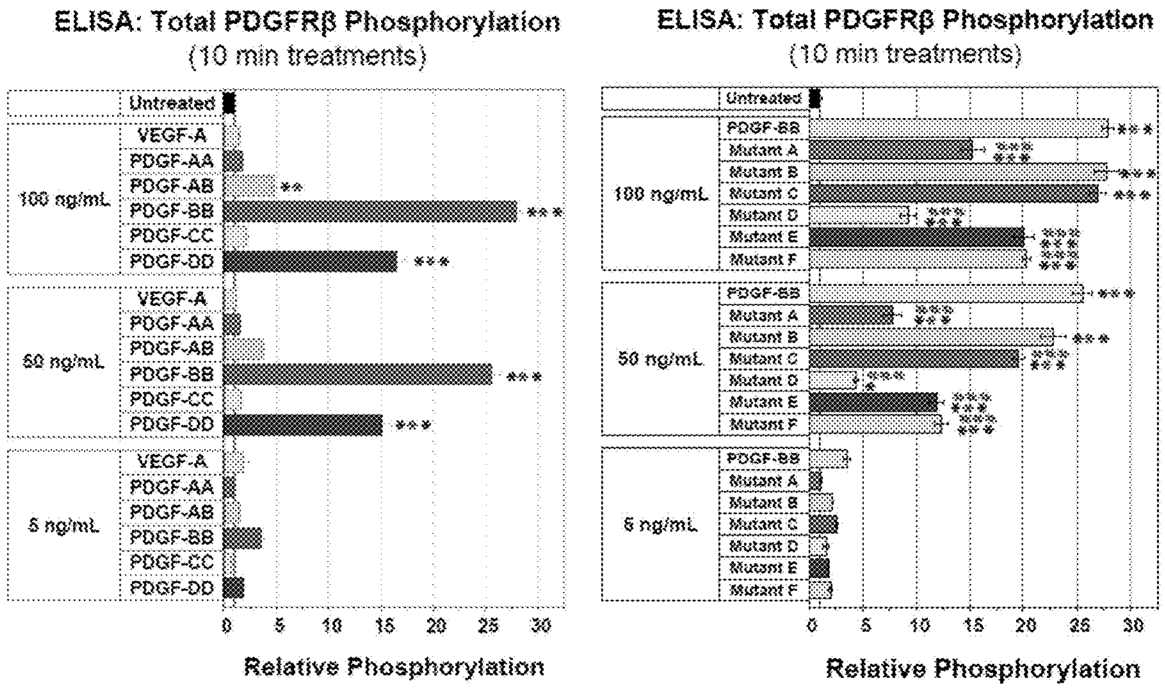
FIG. 15A depicts a human dermal fibroblast (HDF) enzyme-linked immunosorbent (ELISA) assay measuring relative total PDGFRβ phosphorylation after ligand stimulation. * indicates a value significantly different than the untreated condition. # indicates a mutant significantly different from PDGF-BB at the same concentration. * or # indicates $p<0.05$.  or ## indicates $p<0.01$. * or ### indicates $p<0.001$.
Figure 15B:
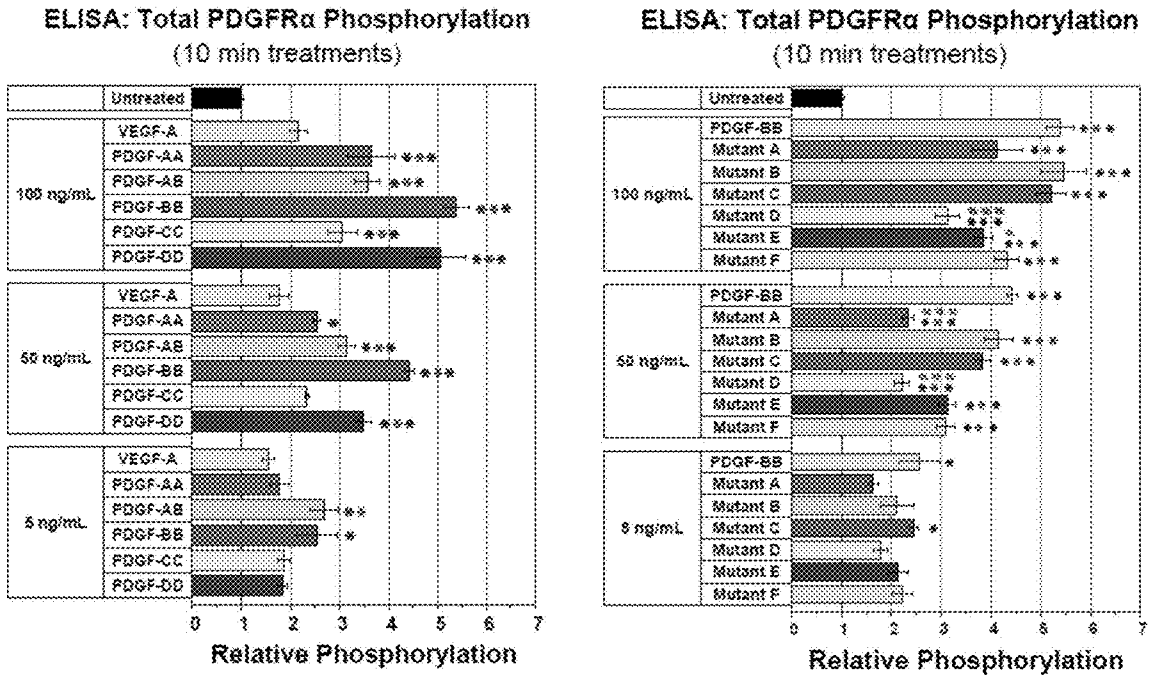
FIG. 15B depicts a human dermal fibroblast (HDF) enzyme-linked immunosorbent (ELISA) assay measuring relative total PDGFRα phosphorylation after ligand stimulation. * indicates a value significantly different than the untreated condition. # indicates a mutant significantly different from PDGF-BB at the same concentration. * or # indicates p<0.05.  or ## indicates p<0.01. * or ### indicates p<0.001.
Figure 16:
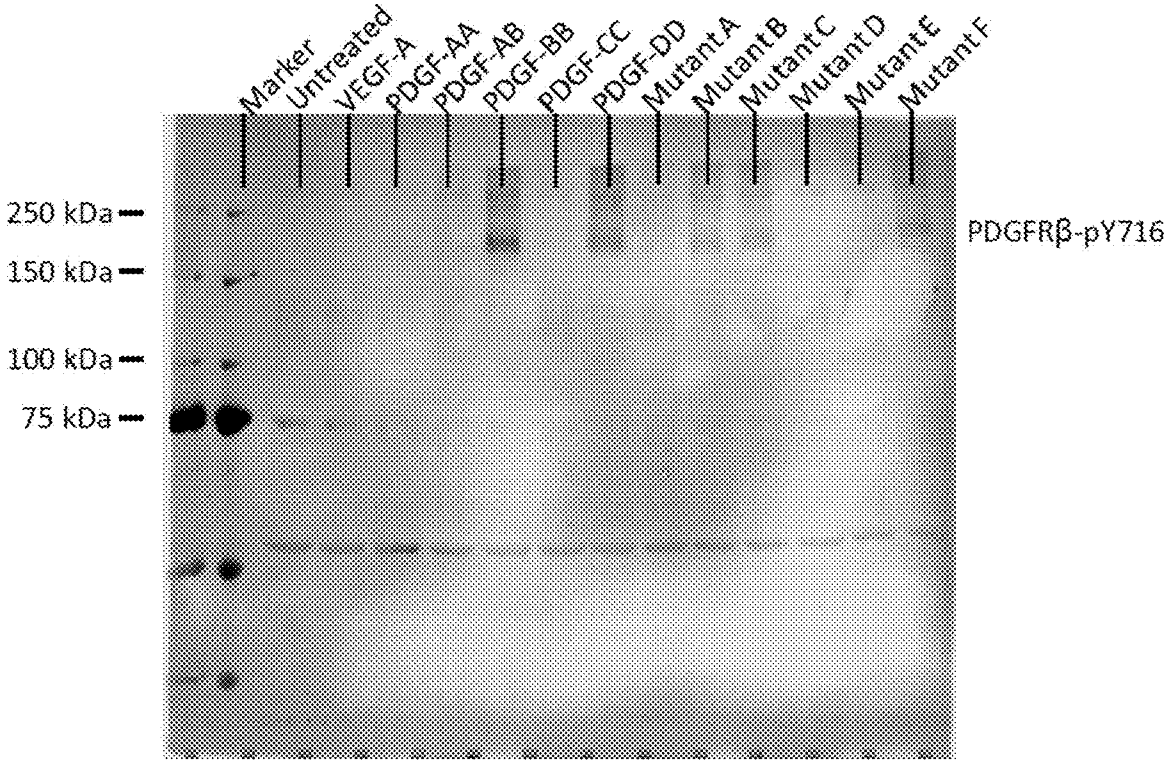
FIG. 16 depicts a Western blot for protein lysates of human dermal fibroblast (HDF) cells after 10 min ligand stimulation probed for PDGFRβ-pY716.
Figure 17:
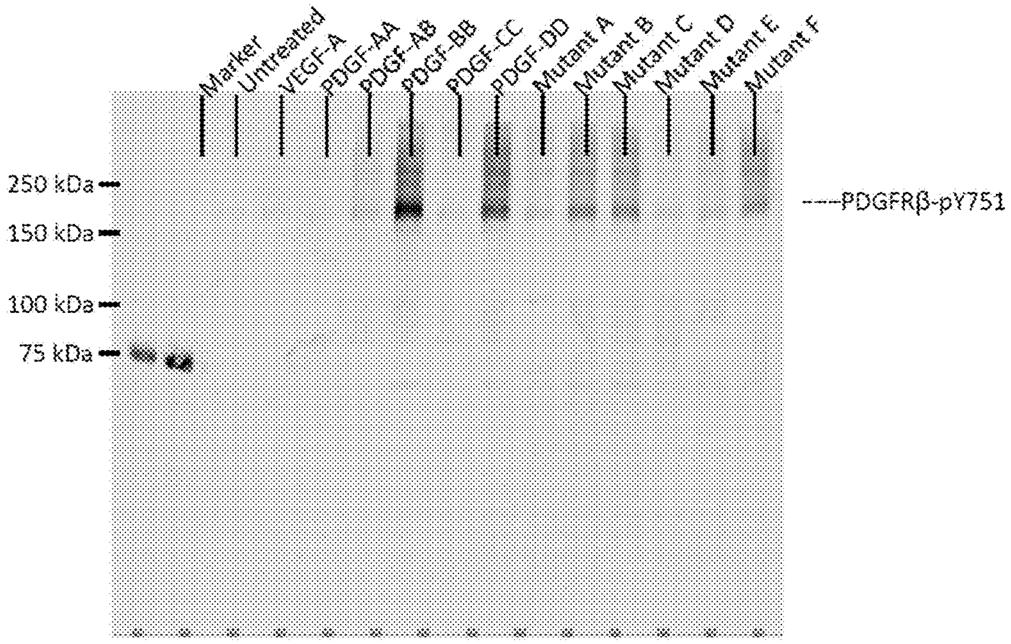
FIG. 17 depicts Western blots for protein lysates of human dermal fibroblast (HDF) cells after 10 min ligand stimulation probed for PDGFRβ-pY751.
Figure 18:
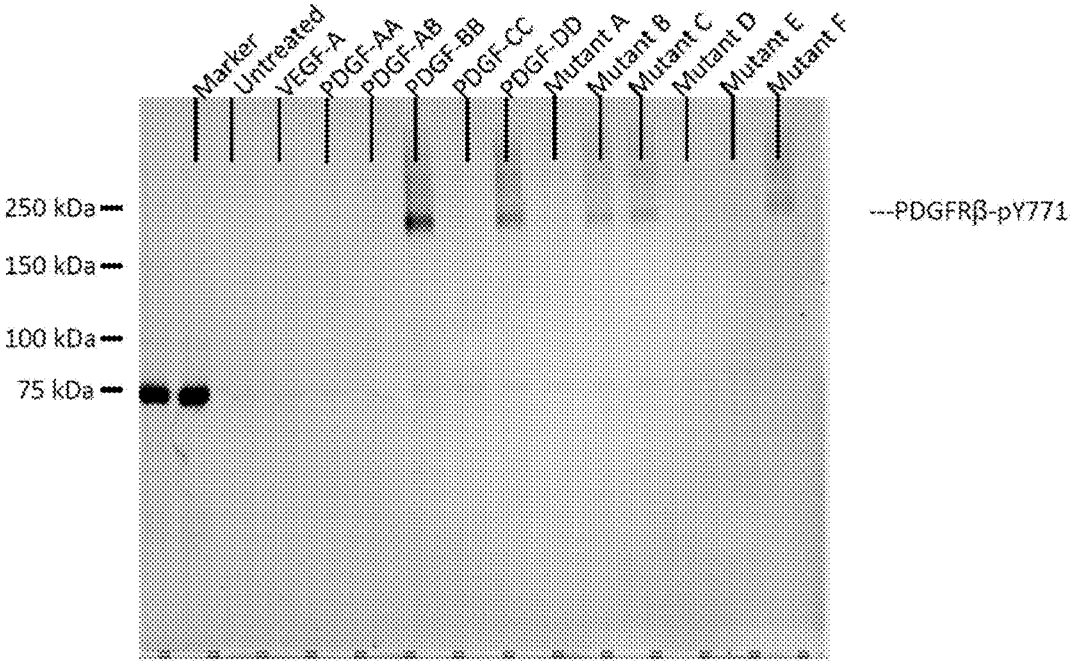
FIG. 18 depicts Western blots for protein lysates of human dermal fibroblast (HDF) cells after 10 min ligand stimulation probed for PDGFRβ-pY771.
Figure 19:
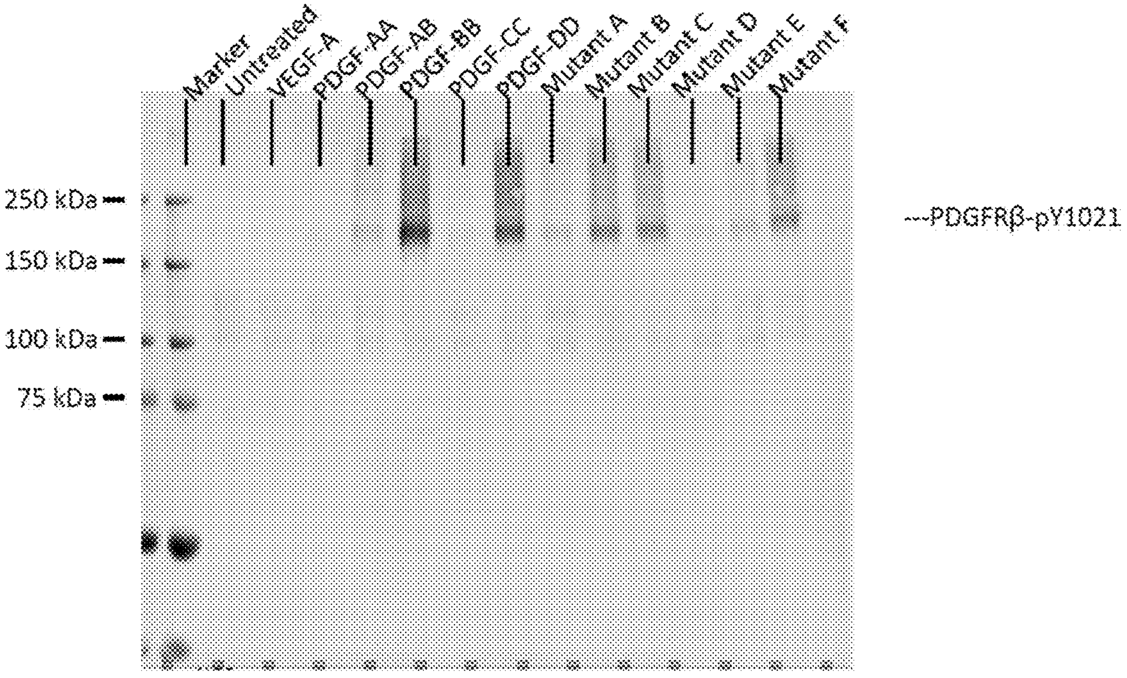
FIG. 19 depicts Western blots for protein lysates of human dermal fibroblast (HDF) cells after 10 min ligand stimulation probed for PDGFRβ-pY1021.

At 50 ng/mL and 100 ng/mL, treatment with PDGF-BB and mutants A-F resulted in more total PDGFRβ and PDGFRα phosphorylation compared to the untreated control (FIG. 15A-15B). This indicates that treatment with wild type or mutant PDGF-B can contribute to increased PDGFR signaling.

Example 7: Western Blots Measuring PDGFR Phosphorylation after Ligand Stimulation Western blots were performed to distinguish important PDGFR phospho-tyrosine sites activated by the tested ligands. HDFs were grown to confluence, incubated for 3 hours with serum-free DMEM, and then treated with individual ligands for 10 minutes before samples were lysed with a cocktail of RIPA lysis buffer (EMD Millipore, Cat. #20-188), phosphatase inhibitors (Sigma-Aldrich, Cat. #4906837001), and protease inhibitors (Sigma-Aldrich, Cat. #11836170001). Sample protein concentrations were estimated using a BCA Protein Assay (Thermo Fisher Scientific, Cat. #23227). SDS-Sample Buffer (Fisher Scientific, Cat. #BP-111R) was added to lysis samples before samples were heated at 95° C. for 10 minutes. We ran 20 μg of each sample through 8% polyacrylamide gels alongside a protein ladder (Bio-Rad, Cat. #161-0374). After gels were run, the protein was transferred from the gels to nitrocellulose membranes (Bio-Rad, Cat. #1620215). The membranes were then blocked with 5% non-fat dry milk before being probed using primary antibodies for p-PDGFRα-Y742 (Thermo Scientific, Cat. #441006), p-PDGFRβ-Y771 (Cell Signaling Technology, Cat. #31735), p-PDGFRβ-Y1021 (R&D Systems, Cat. #AF2316), p-PDGFRβ-Y751 (R&D Systems, Cat. #AF1767), and p-PDGFRβ-Y716 (BioVision, Cat. #A1035). The membranes were then probed with fluorescent secondary antibody (LI-COR Biosciences, Cat. #926-32213) and imaged using a LI-COR Odyssey CLx. Densitometry analysis was performed using the Image Studio™ Acquisition Software.

PDGFRs have multiple tyrosine phosphorylation sites on the C-terminus. For example, PDGFRβ has Y579, Y581, Y716, Y740, Y751, Y763, Y771, Y775, Y1009, and Y1021 sites (in addition to 2 sites in the 2nd kinase region). PDGFRα has 10 C-terminal sites.

While the ELISAs from Example 6 use a pan-phosphorylation kit that reports any phosphorylation obtained from the PDGFR being tested, the Western blots each test only one phosphorylation site.

FIG. 16-FIG. 19 show Western blots probing for various phosphorylated PDGFRβ (pY716, pY751, pY771, and pY1021 respectively). Treatment with PDGF-BB or PDGF-DD ligand resulted in a strong signal for each antibody, indicating PDGFRβ phosphorylation. Of the mutants, mutants B, C, and F produce the strongest signal on each blot. Each of mutants A-F result in some signal for each phosphorylation-specific antibody. The strength of signal for adding a given ligand varies by phosphorylation site probed, indicating different amounts of phosphorylation at different sites.

Figure 20:
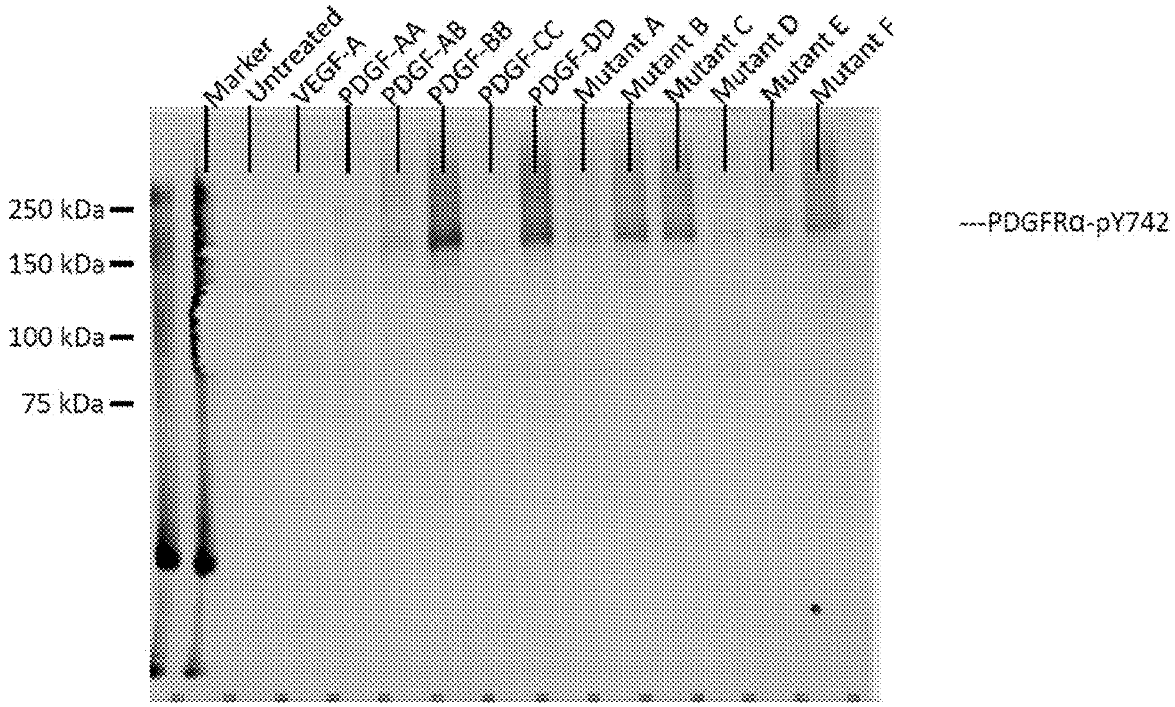
FIG. 20 depicts Western blots for protein lysates of human dermal fibroblast (HDF) cells after 10 min ligand stimulation probed for PDGFRα-pY742.
Figure 21:
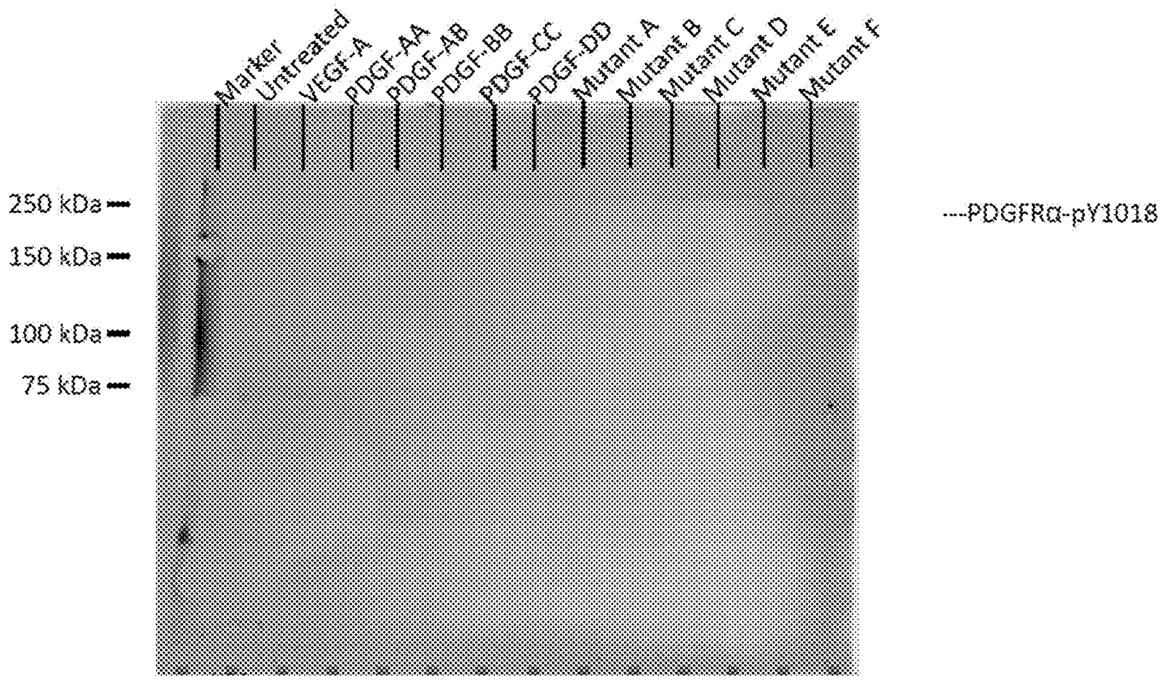
FIG. 21 depicts Western blots for protein lysates of human dermal fibroblast (HDF) cells after 10 min ligand stimulation probed for PDGFRα-Y1018.

FIG. 20-21 show Western blots probing for various phosphorylated PDGFRα (pY742 and pY1018, respectively). Strong signal was produced for pY742 (FIG. 20) but not pY1018 (FIG. 21), indicating variation in PDGFRα phosphorylation at different sites. For pY742 (FIG. 20), signal was visible for each PDGF wild type or mutant ligand. Of the mutants, mutants B, C, and F produce the strongest signal.

Thus, treatment with PDGF ligands and mutants A-F can also increase PDGFR phosphorylation. Each site does not elicit the same amount of phosphorylation. Some sites are strong signaling sites; others produce very little signal at the concentration of ligands tested.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained. As various changes could be made in the above compositions and processes without departing from the scope of the invention, it is intended that all matter contained in the above description and shown in the accompanying drawings shall be interpreted as illustrative and not in a limiting sense.

The invention claimed is:

1. An isolated polypeptide having an amino acid sequence comprising at least about 93% of SEQ ID NO: 1, wherein the polypeptide binds to a PDGF receptor and/or a VEGF receptor and increases PDGF and/or VEGF signaling in the cell, and wherein the polypeptide comprises at least one amino acid substitution resulting in a higher binding affinity to the receptor than a wild-type PDGF or VEGF polypeptide, wherein the at least one amino acid substitution is selected from the group consisting of: M12R, I13E, K17N, E21Y, V22L, E24R, R28N, R32I, N57Y, Q71M, and T101K, and any other amino acid substitutions are conservative amino acid substitutions or selected from the group consisting of 177F and K98R.

2. The isolated polypeptide of claim 1 wherein the polypeptide comprises at least one amino acid substitution at position 13, 17, 21, 22, 24, 28, 32, 57, 71, or 101.

3. The isolated polypeptide of claim 1 wherein the polypeptide has an amino acid sequence comprising at least 95% identity to any one of SEQ ID NOs: 2-9 and 11.

4. A composition for increasing PDGF and/or VEGF signaling in a subject, the composition comprising any polypeptide of claim 1, and a pharmaceutically acceptable carrier.

5. An isolated nucleic acid that encodes for any polypeptide of claim 1.

6. A vector comprising the isolated nucleic acid of claim 5 and a heterologous nucleic acid sequence.

7. A host cell expressing the vector of claim 6.

8. The host cell of claim 7 wherein the host cell comprises a bacterial cell.

9. A method of increasing PDGF and/or VEGF signaling in a cell the method comprising administering the polypeptide of claim 1 to the cell.

10. A method of treating a disease or condition associated with abnormal PDGF and/or VEGF signaling in a subject in need thereof, the method comprising administering the polypeptide of claim 1 to the subject, wherein the disease or condition is associated with insufficient or reduced PDGF and/or VEGF signaling and administering the polypeptide increases PDGF and/or VEGF signaling in the subject.

11. The method of claim 10 wherein the method is for treating wounds and/or enhancing wound healing.

12. The method of claim 11, further comprising administering becaplermin to the subject.

13. An isolated polypeptide having an amino acid sequence, wherein the polypeptide binds to a PDGF receptor and/or a VEGF receptor and increases PDGF and/or VEGF signaling in the cell, wherein the polypeptide has an amino acid sequence comprising any one of SEQ ID NOs: 2-9 and 11.

14. The isolated polypeptide of claim 13 wherein the polypeptide has an amino acid sequence consisting of any one of SEQ ID NOs: 2-9 and 11.

15. A composition for increasing PDGF and/or VEGF signaling in a subject, the composition comprising any polypeptide of claim 13, and a pharmaceutically acceptable carrier.

16. An isolated nucleic acid that encodes for any polypeptide of claim 13.

17. A vector comprising the isolated nucleic acid of claim 16 and a heterologous nucleic acid sequence.

18. A host cell expressing the vector of claim 17.

19. A method of increasing PDGF and/or VEGF signaling in a cell the method comprising administering the polypeptide of claim 18 to the cell.

20. A method of treating a disease or condition associated with abnormal PDGF and/or VEGF signaling in a subject in need thereof, the method comprising administering the polypeptide of claim 13 to the subject, wherein the disease or condition is associated with insufficient or reduced PDGF and/or VEGF signaling and administering the polypeptide increases PDGF and/or VEGF signaling in the subject.

* * * * *